United States Patent
McNair

(10) Patent No.: US 11,857,477 B1
(45) Date of Patent: *Jan. 2, 2024

(54) PRESSURE INJURY PREVENTION SENSOR AND DECISION SUPPORT TOOL

(71) Applicant: CERNER INNOVATION, INC., Kansas City, KS (US)

(72) Inventor: Douglas S. McNair, Seattle, WA (US)

(73) Assignee: Cerner Innovation, Inc., Kansas City, MO (US)

(*) Notice: Subject to any disclaimer, the term of this patent is extended or adjusted under 35 U.S.C. 154(b) by 1111 days.

This patent is subject to a terminal disclaimer.

(21) Appl. No.: 16/575,094

(22) Filed: Sep. 18, 2019

Related U.S. Application Data

(60) Provisional application No. 62/785,089, filed on Dec. 26, 2018, provisional application No. 62/733,071, filed on Sep. 18, 2018.

(51) Int. Cl.
| | | |
|---|---|---|
| *A61G 7/057* | (2006.01) | |
| *A61B 5/00* | (2006.01) | |
| *A61B 5/11* | (2006.01) | |

(52) U.S. Cl.
CPC ........ *A61G 7/05769* (2013.01); *A61B 5/1116* (2013.01); *A61B 5/447* (2013.01);
(Continued)

(58) Field of Classification Search
CPC ............ A61G 7/05769; A61G 2203/44; A61B 5/1116; A61B 5/447; A61B 5/6892; A61B 2562/046; G01R 23/16; G06F 17/14
See application file for complete search history.

(56) References Cited

U.S. PATENT DOCUMENTS

| | | |
|---|---|---|
| 4,175,263 A | 11/1979 | Morrow et al. |
| 5,819,349 A | 10/1998 | Schwartz |

(Continued)

FOREIGN PATENT DOCUMENTS

| | | | | |
|---|---|---|---|---|
| GB | 2558614 A | 7/2018 | | |
| WO | WO-2011113070 A1 * | 9/2011 | ............... | A41B 9/00 |

(Continued)

OTHER PUBLICATIONS

Wikipedia.com, "Colors of Noise", May 28, 2018, accessed from archive.org on Feb. 21, 2023 (Year: 2018).*

*Primary Examiner* — Myles A Throop
(74) *Attorney, Agent, or Firm* — Invoke

(57) ABSTRACT

Technologies are provided for determining a likelihood or risk of a human patient for developing pressure injury based on patterns of movement by the patient determined using a specialized measurement support surface. Some embodiments automatically ascertain whether patterns of movements of a human subject, whose weight is supported on the support surface, exhibit sufficient frequency and variability of activity such as will confer either certain health benefits or expose the individual to certain health risks, such as development of pressure ulcers in the load-bearing skin and soft tissues. If the determined patterns manifest such features associated with benefits or risks, then a notification may be provided for the patient to move; for instance, to the patient or a caregiver. In some embodiments, a notification may be provided at an irregular time intervals within-day intervals.

20 Claims, 29 Drawing Sheets

(52) U.S. Cl.
CPC .... *A61B 5/6892* (2013.01); *A61B 2562/0247* (2013.01); *A61B 2562/046* (2013.01); *A61G 2203/44* (2013.01)

(56) References Cited

U.S. PATENT DOCUMENTS

| | | | |
|---|---|---|---|
| 6,721,980 B1* | 4/2004 | Price | A61B 5/11 |
| | | | 5/713 |
| 7,120,952 B1 | 10/2006 | Bass et al. | |
| 8,444,558 B2 | 5/2013 | Young et al. | |
| 8,973,186 B2* | 3/2015 | Bhai | A61G 7/05769 |
| | | | 5/616 |
| 9,559,417 B1* | 1/2017 | Schwarzwalder | H01Q 3/2605 |
| 10,553,320 B1* | 2/2020 | McNair | G16H 10/60 |
| 10,586,617 B1 | 3/2020 | Mcnair | |
| 10,786,168 B2* | 9/2020 | Brown | A61B 5/316 |
| 11,278,246 B1* | 3/2022 | McNair | A61B 5/0816 |
| 2005/0190065 A1* | 9/2005 | Ronnholm | G04G 21/025 |
| | | | 340/575 |
| 2007/0276275 A1* | 11/2007 | Proctor | A61B 5/4076 |
| | | | 600/513 |
| 2008/0189865 A1* | 8/2008 | Bhai | A61G 7/05769 |
| | | | 5/706 |
| 2009/0060266 A1* | 3/2009 | Sornborger | G06K 9/00523 |
| | | | 708/424 |
| 2009/0222144 A1* | 9/2009 | Venkatasubramanian | |
| | | | G01R 19/2513 |
| | | | 708/404 |
| 2010/0170043 A1 | 7/2010 | Young et al. | |
| 2010/0268122 A1 | 10/2010 | Drennan et al. | |
| 2011/0010014 A1* | 1/2011 | Oexman | A47C 31/123 |
| | | | 600/301 |
| 2012/0139732 A1 | 6/2012 | Smith et al. | |
| 2016/0049062 A1 | 2/2016 | Campbell | |
| 2016/0256116 A1* | 9/2016 | Baik | A61B 5/0059 |
| 2017/0273611 A1* | 9/2017 | Purdon | A61B 5/24 |
| 2019/0049322 A1 | 2/2019 | James et al. | |
| 2019/0192744 A1* | 6/2019 | Greener | A61F 13/00068 |
| 2021/0316144 A1* | 10/2021 | Ganguly | A61B 5/4836 |
| 2021/0321928 A1* | 10/2021 | Koch | A61B 5/4088 |
| 2021/0401298 A1* | 12/2021 | Levi | A61B 5/7225 |
| 2022/0211318 A1* | 7/2022 | Yan | A61B 5/384 |
| 2022/0240783 A1* | 8/2022 | Fan | A61B 5/02007 |

FOREIGN PATENT DOCUMENTS

| | | | | |
|---|---|---|---|---|
| WO | WO-2012114298 A2 * | 8/2012 | | A61B 5/002 |
| WO | 2018/130824 A1 | 7/2018 | | |

* cited by examiner

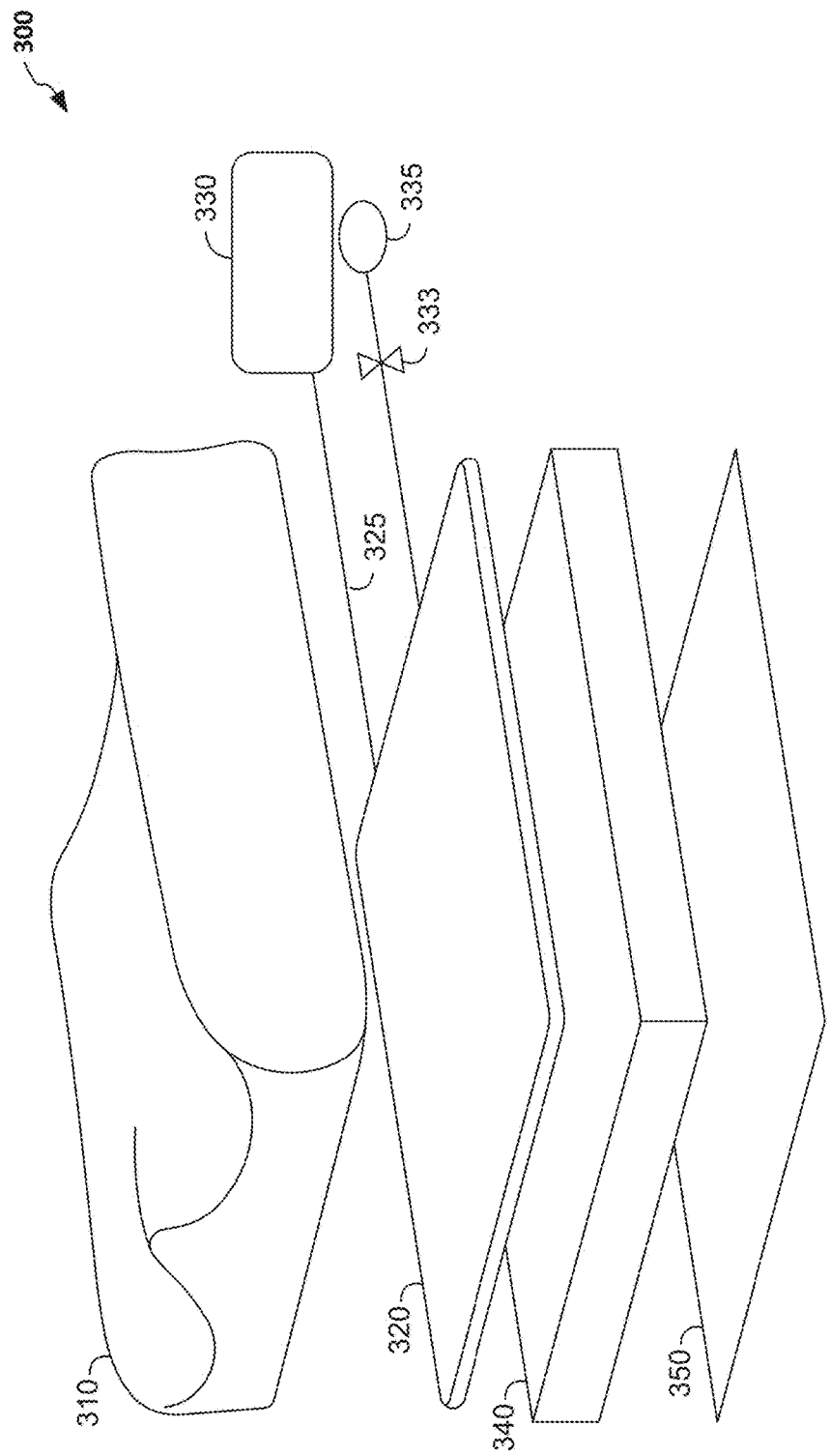

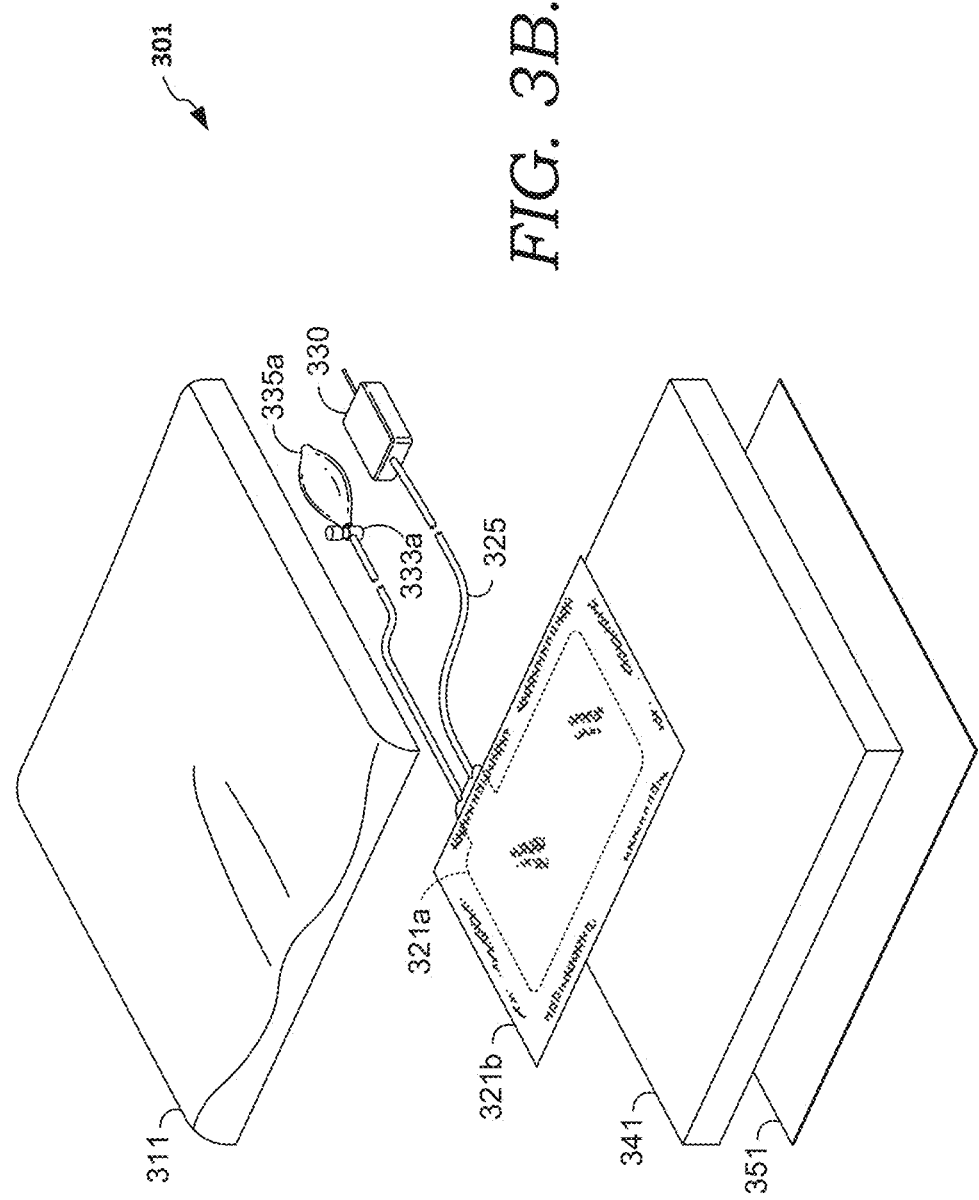

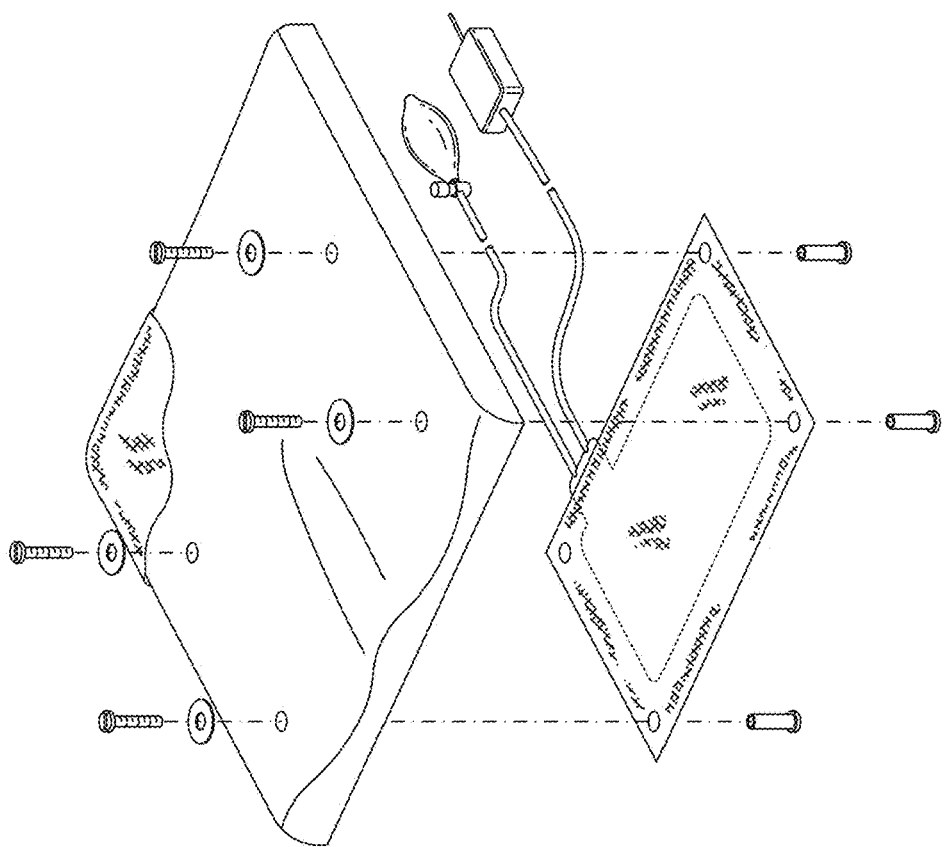
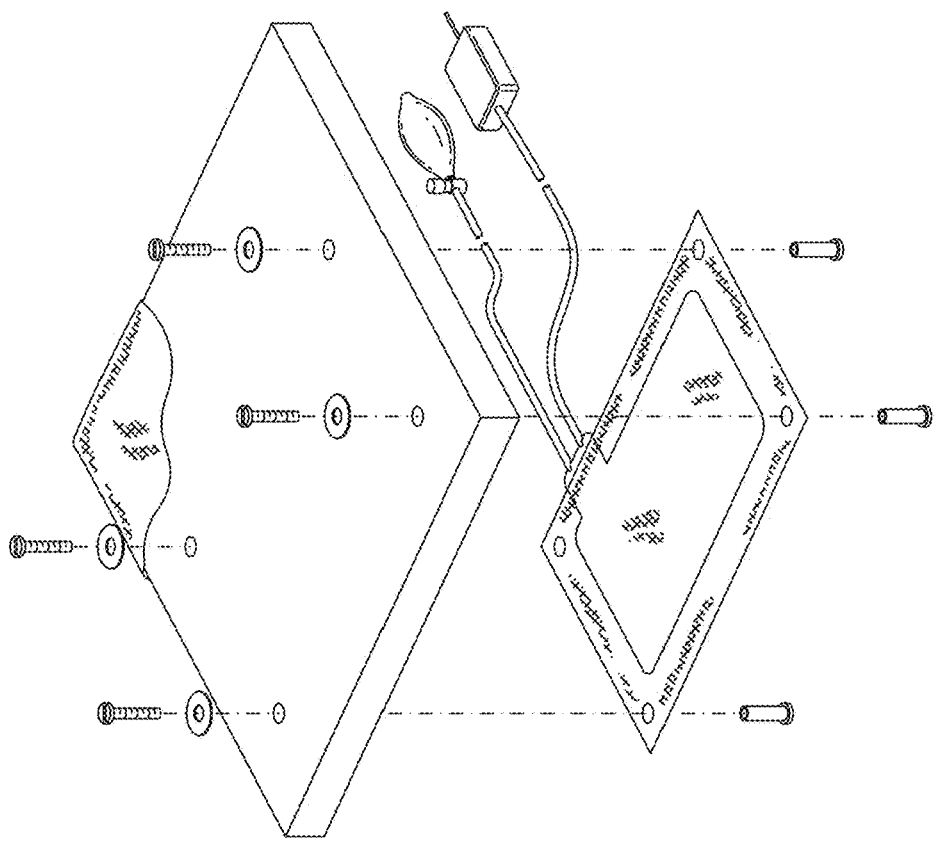
FIG. 3F.

```
###########################################################

#   Power spectral density of cushion pressure time series

##################################################### library(psd)
library(RColorBrewer)
library(segmented)

# load data -- x1 and x2 are the cases and controls
x1 <- read.csv(file="c:/0_cerdsm/0__math_models/pressure_ulcer/data/amb_01.csv", header=FALSE,
        colClasses=rep("numeric",2))
x2 <- read.csv(file="c:/0_cerdsm/0__math_models/pressure_ulcer/data/dsm_01.csv", header=FALSE,
        colClasses=rep("numeric",2))

# calculate multi-taper power spectra
pu <- pspectrum(x1[,2], plot=FALSE)
norm <- pspectrum(x2[,2], plot=FALSE)

# normalize to amplitude at DC (freq = 0)
len <- length(norm$spec)

max1 <- pu$spec[1]
pu1 <- matrix(rep(0,2*len-2), ncol=2, dimnames=list(rownames=NULL, colnames=c("logfreq", "logspec")),
    byrow=FALSE)
pu1[,1] <- log10(pu$freq[2:len])
pu1[,2] <- log10(pu$spec[2:len]/max1)
pu1 <- pu1[41:1200,]

max1 <- norm$spec[1]
norm1 <- matrix(rep(0,2*len-2), ncol=2, dimnames=list(rownames=NULL, colnames=c("logfreq", "logspec")),
    byrow=FALSE)
norm1[,1] <- log10(norm$freq[2:len])
norm1[,2] <- log10(norm$spec[2:len]/max1)
norm1 <- norm1[41:1200,]

# plot the PU and normal spectra for bandwidth between 0.001 and 0.03 Hz
plot(pu1[,1], pu1[,2], main="Cushion Pressure Spectra, Pressure Ulcer vs. Normal",
    lwd=3, col="red", ty="l", xlim=c(-3.0,-1.5), ylim=c(-3.0,-1.0), xlab="log(freq)", ylab="dB")
lines(norm1[,1], norm1[,2], lwd=3, lty=5, col="blue")
text(c(-2.5,-2.2), c(-2.2,-1.5), c("PU","Normal"), cex=1)

# identify segments (if any) in PU spectrum
z <- pu1[,1]
len <- length(z)

o <- lm(pu1[,2] ~ z)
l.seg <- segmented(o, seg.Z=~z, psi=-2.9)
l.seg$coefficients[1:2] # left line segment
#   (Intercept)     z
-5.97864      -1.56226   brown noise at lower freq, left-shifted from normal rt <- length(which(l.seg$model[,3] == 0))
r.seg <- lm(pu1[rt:len,2] ~ pu1[rt:len,1])
r.seg$coefficients     # right line segment
#   (Intercept)     z
#   -2.34902      -0.15739   white noise at higher freq
```

*FIG. 7A.*

CONTINUES IN FIG. 7B

CONTINUES FROM FIG. 7A

```
plot(pu1[,1], pu1[,2], main="Cushion Pressure Spectrum, Pressure Ulcer",
    lwd=3, col="red", ty="l", xlim=c(-3.0,-1.5), ylim=c(-3.0,-1.0), xlab="log(freq)", ylab="dB")
# abline(r.seg$coefficients, col="red", lwd=2)
plot(l.seg, add=TRUE, lwd=2, col="red", lty=2, link=FALSE)
points(l.seg, col=1, lwd=4, cex=2.5, link=FALSE)

# identify segments (if any) in normal spectrum
z <- norm1[,1]
len <- length(z)

o <- lm(norm1[,2] ~ z)
l.seg <- segmented(o, seg.Z=~z, psi=-2.9)
l.seg$coefficients[1:2] # left line segment
#   (Intercept)        z
-4.01527   -1.01467    pink noise at lower freq rt <- length(which(l.seg$model[,3] == 0))
r.seg <- lm(norm1[rt:len,2] ~ norm1[rt:len,1])
r.seg$coefficients    # right line segment
#   (Intercept)        z
-5.19622   -1.61396    brown noise at higher freq plot(norm1[,1], norm1[,2], main="Cushion Pressure Spectrum, Normal",
    lwd=3, col="blue", ty="l", xlim=c(-3.0,-1.5), ylim=c(-3.0,-1.0), xlab="log(freq)", ylab="dB")
# abline(r.seg$coefficients, col="blue", lwd=2)
plot(l.seg, add=TRUE, lwd=2, col="blue", lty=2, link=FALSE)
points(l.seg, col=1, lwd=4, cex=2.5, link=FALSE)
```

*FIG. 7B.*

```
###########################################################

#   Power spectral density of cushion pressure time series

##################################################### library(psd)
library(RColorBrewer)
library(segmented)

# load data -- x1 and x2 are the cases and controls
x1 <- read.csv(file="c:/0_cerdsm/0__math_models/pressure_ulcer/data/amb_02.csv", header=FALSE,
        colClasses=rep("numeric",2))
x2 <- read.csv(file="c:/0_cerdsm/0__math_models/pressure_ulcer/data/dsm_02.csv", header=FALSE,
        colClasses=rep("numeric",2))

# calculate multi-taper power spectra
pu <- pspectrum(x1[,2], plot=FALSE)
norm <- pspectrum(x2[,2], plot=FALSE)

# normalize to amplitude at DC (freq = 0)
len <- length(norm$spec)

max1 <- pu$spec[1]
pu1 <- matrix(rep(0,2*len-2), ncol=2, dimnames=list(rownames=NULL, colnames=c("logfreq", "logspec")),
byrow=FALSE)
pu1[,1] <- log10(pu$freq[2:len])
pu1[,2] <- log10(pu$spec[2:len]/max1)
pu1 <- pu1[41:1200,]

max1 <- norm$spec[1]
norm1 <- matrix(rep(0,2*len-2), ncol=2, dimnames=list(rownames=NULL, colnames=c("logfreq", "logspec")),
byrow=FALSE)
norm1[,1] <- log10(norm$freq[2:len])
norm1[,2] <- log10(norm$spec[2:len]/max1)
norm1 <- norm1[41:1200,]

# plot the PU and normal spectra for bandwidth between 0.001 and 0.03 Hz
plot(pu1[,1], pu1[,2], main="Cushion Pressure Spectra, Pressure Ulcer vs. Normal",
    lwd=3, col="red", ty="l", xlim=c(-3.0,-1.5), ylim=c(-3.0,-1.0), xlab="log(freq)", ylab="dB")
lines(norm1[,1], norm1[,2], lwd=3, lty=5, col="blue")
text(c(-2.5,-2.1), c(-2.2,-1.4), c("PU","Normal"), cex=1)

# identify segments (if any) in PU spectrum
z <- pu1[,1]
len <- length(z)

o <- lm(pu1[,2] ~ z)
l.seg <- segmented(o, seg.Z=~z, psi=-2.9)
l.seg$coefficients[1:2]  # left line segment
#    (Intercept)        z
-4.57234   -1.09408    pink noise at lower freq, left-shifted from normal rt <- length(which(l.seg$model[,3] == 0))
r.seg <- lm(pu1[rt:len,2] ~ pu1[rt:len,1])
r.seg$coefficients     # right line segment
#    (Intercept)        z
#       -2.38011   -0.18062    white noise at higher freq
```

*FIG. 8A.*

CONTINUES IN FIG. 8B

CONTINUES FROM FIG. 8A

```
plot(pu1[,1], pu1[,2], main="Cushion Pressure Spectrum, Pressure Ulcer",
    lwd=3, col="red", ty="l", xlim=c(-3.0,-1.5), ylim=c(-3.0,-1.0), xlab="log(freq)", ylab="dB")
# abline(r.seg$coefficients, col="red", lwd=2)
plot(l.seg, add=TRUE, lwd=2, col="red", lty=2, link=FALSE)
points(l.seg, col=1, lwd=4, cex=2.5, link=FALSE)

# identify segments (if any) in normal spectrum
z <- norm1[,1]
len <- length(z)

o <- lm(norm1[,2] ~ z)
l.seg <- segmented(o, seg.Z=~z, psi=-2.9)
l.seg$coefficients[1:2] # left line segment
#   (Intercept)      z
-4.11944   -1.138093    pink noise at lower freq rt <- length(which(l.seg$model[,3] == 0))
r.seg <- lm(norm1[rt:len,2] ~ norm1[rt:len,1])
r.seg$coefficients    # right line segment
#   (Intercept)      z
-7.04409   -2.61435    black noise at higher freq plot(norm1[,1], norm1[,2], main="Cushion Pressure Spectrum, Normal",
    lwd=3, col="blue", ty="l", xlim=c(-3.0,-1.5), ylim=c(-3.0,-1.0), xlab="log(freq)", ylab="dB")
# abline(r.seg$coefficients, col="blue", lwd=2)
plot(l.seg, add=TRUE, lwd=2, col="blue", lty=2, link=FALSE)
points(l.seg, col=1, lwd=4, cex=2.5, link=FALSE)
```

*FIG. 8B.*

```
################################################

#   Power spectral density of cushion pressure time series

########################################## library(psd)
library(RColorBrewer)
library(segmented)

# load data -- x1 and x2 are the cases and controls
x1 <- read.csv(file="c:/0_cerdsm/0__math_models/pressure_ulcer/data/amb_03.csv", header=FALSE,
        colClasses=rep("numeric",2))
x2 <- read.csv(file="c:/0_cerdsm/0__math_models/pressure_ulcer/data/dsm_03.csv", header=FALSE,
        colClasses=rep("numeric",2))

# calculate multi-taper power spectra
pu <- pspectrum(x1[,2], plot=FALSE)
norm <- pspectrum(x2[,2], plot=FALSE)

# normalize to amplitude at DC (freq = 0)
len <- length(norm$spec)

max1 <- pu$spec[1]
pu1 <- matrix(rep(0,2*len-2), ncol=2, dimnames=list(rownames=NULL, colnames=c("logfreq", "logspec")),
    byrow=FALSE)
pu1[,1] <- log10(pu$freq[2:len])
pu1[,2] <- log10(pu$spec[2:len]/max1)
pu1 <- pu1[41:1200,]

max1 <- norm$spec[1]
norm1 <- matrix(rep(0,2*len-2), ncol=2, dimnames=list(rownames=NULL, colnames=c("logfreq", "logspec")),
    byrow=FALSE)
norm1[,1] <- log10(norm$freq[2:len])
norm1[,2] <- log10(norm$spec[2:len]/max1)
norm1 <- norm1[41:1200,]

# plot the PU and normal spectra for bandwidth between 0.001 and 0.03 Hz
plot(pu1[,1], pu1[,2], main="Cushion Pressure Spectra, Pressure Ulcer vs. Normal",
    lwd=3, col="red", ty="l", xlim=c(-3.0,-1.5), ylim=c(-3.0,-1.0), xlab="log(freq)", ylab="dB")
lines(norm1[,1], norm1[,2], lwd=3, lty=5, col="blue")
text(c(-2.5,-2.2), c(-2.2,-1.5), c("PU","Normal"), cex=1)

# identify segments (if any) in PU spectrum
z <- pu1[,1]
len <- length(z)

o <- lm(pu1[,2] ~ z)
l.seg <- segmented(o, seg.Z=~z, psi=-2.9)
l.seg$coefficients[1:2]   # left line segment
#     (Intercept)        z
-3.00616     -0.40167    pink noise at lower freq, left-shifted from normal rt <- length(which(l.seg$model[,3] == 0))
r.seg <- lm(pu1[rt:len,2] ~ pu1[rt:len,1])
r.seg$coefficients       # right line segment
#     (Intercept)        z
#       -2.44023     -0.13997    white noise at higher freq
```

*FIG. 9A.*

CONTINUES IN FIG. 9B

CONTINUES FROM FIG. 9A

```
plot(pu1[,1], pu1[,2], main="Cushion Pressure Spectrum, Pressure Ulcer",
    lwd=3, col="red", ty="l", xlim=c(-3.0,-1.5), ylim=c(-3.0,-1.0), xlab="log(freq)", ylab="dB")
# abline(r.seg$coefficients, col="red", lwd=2)
plot(l.seg, add=TRUE, lwd=2, col="red", lty=2, link=FALSE)
points(l.seg, col=1, lwd=4, cex=2.5, link=FALSE)

# identify segments (if any) in normal spectrum
z <- norm1[,1]
len <- length(z)

o <- lm(norm1[,2] ~ z)
l.seg <- segmented(o, seg.Z=~z, psi=-2.9)
l.seg$coefficients[1:2] # left line segment
#   (Intercept)      z
-5.32662   -1.38370    pink noise at lower freq rt <- length(which(l.seg$model[,3] == 0))
r.seg <- lm(norm1[rt:len,2] ~ norm1[rt:len,1])
r.seg$coefficients    # right line segment
#   (Intercept)      z
-6.97280   -2.13595    black noise at higher freq plot(norm1[,1], norm1[,2], main="Cushion Pressure Spectrum, Normal",
    lwd=3, col="blue", ty="l", xlim=c(-3.0,-1.5), ylim=c(-3.0,-1.0), xlab="log(freq)", ylab="dB")
# abline(r.seg$coefficients, col="blue", lwd=2)
plot(l.seg, add=TRUE, lwd=2, col="blue", lty=2, link=FALSE)
points(l.seg, col=1, lwd=4, cex=2.5, link=FALSE)
```

*FIG. 9B.*

```
################################################

#   Generate receiver operating characteristic (ROC) curve of PU prediction

########################################## library(pROC)

load data
ds4 <- read.csv(file="c:/0_cerdsm/0__math_models/pressure_ulcer/pu_roc.csv")
roc1 <- roc(ds4[,1] ~ ds4[,2], percent=TRUE,
# arguments for auc
# partial.auc=c(100, 90), partial.auc.correct=TRUE,
# partial.auc.focus="sens",
# arguments for ci
  ci=TRUE, boot.n=100, ci.alpha=0.9, stratified=FALSE,
# arguments for plot
# auc.polygon=TRUE, max.auc.polygon=TRUE,
  plot=TRUE, grid=TRUE, print.auc=TRUE, show.thres=TRUE)
sens.ci <- ci.se(roc1, specificities=seq(0, 100, 5))
plot(sens.ci, type="shape", col="lightblue")
plot(sens.ci, type="bars")

roc(ds4[,1] ~ ds4[,2], ds4, plot=TRUE, col="red")

# column-major
dsm <- matrix(c(4,1,0,11), ncol=2)
fisher.test(dsm)
```

*FIG. 10.*

STAGES OF PRESSURE ULCERS

PRESSURE INJURY PREVENTION SENSOR AND DECISION SUPPORT TOOL

RELATED APPLICATIONS

This non-provisional patent application claims priority benefit to provisional patent application No. 62/733,071, entitled "Pressure Injury Prevention Sensor and Decision Support Tool," filed on Sep. 18, 2018, and incorporated by reference herein in its entirety. This non-provisional patent application also claims priority benefit to provisional patent application No. 62/785,089, entitled "Pressure Injury Prevention Sensor and Decision Support Tool," filed on Dec. 26, 2018, which is also incorporated by reference herein in its entirety.

BACKGROUND

The development of a pressure ulcer (also called pressure injury) has been considered an indicator for quality of care, as pressure ulcers are potentially preventable, a leading cause of morbidity for inpatients, and a cause of substantial discomfort, prolonged hospitalizations, additional healthcare costs and, in some cases, death. The National Pressure Ulcer Advisory Panel defines a pressure ulcer as 'a localized injury to the skin and/or underlying tissue over a bony prominence, as a result of pressure, or pressure in combination with shear. The severity of pressure ulcers can vary from skin erythema to full-thickness tissue loss, with damage extending to the muscle and bone. It is estimated that pressure ulcers affect 250,000 to 500,000 patients at any time, with an annual prevalence of 21%-26% in healthcare institutions in North America. In the USA, pressure ulcer prevalence ranged from 10% to 18% in general acute care, 2.3% to 28% in long-term care and 0% to 29% in home care between 1990 and 2000. The Global Burdent of Disease ("GBD") Morbidity and Mortality project recently determined that pressure ulcers are associated with 0.66 million disability-adjusted life-years ("DALYs") (at a 95% confidence interval: 0.55 to 0.78) worldwide, which does not take into account supervening sepsis or other life-threatening sequellae.

In a recent review of international studies, pressure ulcer prevalence in acute care was estimated at 6% to 18.5%. As more severe cases require intensive treatments, have a prolonged healing time and are associated with higher incidence of complications, the estimated cost of treatment varies from £1,214 to £14,108 per case in the U.K. and $124,327 to $129,248 in the U.S. for stage IV pressure ulcers. In Canada, the estimated average monthly cost of pressure ulcer management among individuals with a spinal cord injury was $4,475 in 2010. To date, information about pressure ulcers has been primarily obtained through cross-sectional surveys, incident reports and chart reviews. Surveys, incident reports and reporting systems, such as the National Health Service National Safety Thermometer in the UK, involve voluntary reporting which can result in inaccurate and under-reported data. The medical chart has been considered the 'reference standard' as a source of research and quality improvement data due to the clinical information it contains. Thus, retrospective reviews of medical records have been undertaken to identify patient characteristics and associated risk factors among various patient populations, evaluate preventive and management strategies and evaluate the Braden scale in assessing risk for pressure ulcer development.

On account of these financial, clinical, and human quality-of-life aspects, it is therefore of considerable value to have the improved technologies, as described in the present disclosure, of determining and predicting a risk of pressure injury to load-bearing tissues in contact with support surfaces, not only for preventing the development of new pressure ulcers but also for appropriately treating and escalating interventions with regard to existing pressure ulcers—so that the time to healing of such wounds can be shortened; so that infection and sepsis and other complications can be averted; and so that healing can be achieved in a higher percentage of cases. Moreover, while there have been attempts to provide technological solutions through decision support systems and sensor technologies, these systems have significant drawbacks and cannot provide the reliability and accuracy of the systems and processes proposed in the present disclosure.

SUMMARY

This summary is provided to introduce a selection of concepts in a simplified form that are further described below in the detailed description. This summary is not intended to identify key features or essential features of the claimed subject matter, nor is it intended to be used in isolation as an aid in determining the scope of the claimed subject matter.

Technologies described herein may be utilized to determine a likelihood or risk of a human patient for developing pressure injury (such as pressure ulcers or decubitus ulcers), based on patterns of movement by a human patient determined using a support surface. In particular, improved sensor, monitoring and decision support technology is provided for human patients who may be prone to such pressure injury, including technologies for preventive and rehabilitation medicine and physical therapy pertaining to skin and soft tissue integrity and the avoidance and healing of pressure injury. Some embodiments automatically ascertain whether patterns of movements of a human subject, whose weight is supported on the support surface, exhibit sufficient frequency and variability of activity such as will confer either certain health benefits or expose the individual to certain health risks, such as development of pressure ulcers in the load-bearing skin and soft tissues. If the determined patterns manifest such features associated with benefits or risks, then a notification may be provided for the patient to move; for instance, to the patient or a caregiver. In some embodiments, a notification may be provided at irregular time intervals within-day intervals. In this way, healthy patterns of movement and pressure-relief from the load-bearing tissues in contact with the seating support surface are more likely to be established or restored.

According to an embodiment, measurements of pressure associated with mechanical loading of a support surface by suprajacent body parts of a person may be used to determine patterns of load-bearing and moment-to-moment adjustments of position. In one embodiment, a time series of these measurements are determined (or may be received) and used to further determine frequency power spectra for a set of time-periods. In some embodiments, the set of time-periods may comprise contiguous or substantially contiguous time intervals. For a first time-period in the set, such as the current time-period or the most recent time-period, a multi-taper filtered power spectral density is determined over a select frequency band. The power spectrum for these band frequencies then may be normalized, and the resulting pressure power spectrum for the first time-period may transformed as a log-log matrix. For instance, in an embodiment it may be transformed with spectral density in dB for each value of log 10(frequency).

A segmented linear regression of this log-transformed power spectra then may be computed and an optimal cut-point may be determined separating the line-segments. The first-order (slope) coefficient for the segments' linear regressions are then compared to characteristic white-, pink-, brown-, and black-noise $\alpha$ values for $1/f^\alpha$ power roll-off. Based on this comparison, it may be determined that the time-period has conditions for forming pressure-ulcers. The regression coefficients for previous (or prior) time-periods' determine pressure spectra may be used to determine a duty-cycle of patterns whose frequency spectra are associated with pressure ulcer proneness. Where the duty cycle of the high-frequency pressure-ulcer-prone white-noise spectrum condition exceeds a threshold value, then it may be inferred that tissue breakdown occurs and pressure ulcers are likely to form. Similarly, if pressure ulcers are already present in the affected skin and soft tissue, the pressure ulcers are unlikely to heal. In one embodiment, a notification may be provided or another intervening action may be invoked. In this way, some embodiments of the technologies disclosed herein may be configured to operate as an improved sensor as well as providing monitoring and decision support for patients prone to pressure injury.

BRIEF DESCRIPTION OF THE DRAWINGS

The present invention is described in detail below with reference to the attached drawing figures, wherein:

FIGS. 3A-3G depict aspects of one embodiment of a pressure measurement device, in accordance with an embodiment of the disclosure;

FIGS. 7A-9B illustratively provide an example embodiments of computer program routines for determining power spectral density of cushion pressure time series in accordance with an embodiment of the disclosure described in connection to the method of FIG. 2;

FIG. 10 illustratively provides an example embodiment of a computer program routine for generating a receiver operating characteristic (ROC) curve of an embodiment of the pressure ulcer prediction system and method disclosed herein, and described in connection to the method of FIG. 2;

DETAILED DESCRIPTION

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described.

As one skilled in the art will appreciate, embodiments of our invention may be embodied as, among other things: a method, system, or set of instructions embodied on one or more computer readable media, which is described herein. Accordingly, the embodiments may take the form of a hardware embodiment, a software embodiment, or an embodiment combining software and hardware. In one embodiment, the invention takes the form of a computer-program product that includes computer-usable instructions embodied on one or more computer readable media.

Figure 11:
FIG. 11 depicts examples of various stages of pressure ulcers on human patients.

At a high level, this disclosure describes, among other things, improved methods and systems for reducing pressure injury, such as pressure ulcers, in a human patient, which may include improvements in technologies to detect that current conditions of a human patient are likely to result in such injury and initiating an intervening action so that such injury can be averted. Examples of various stages of pressure ulcer injuries are depicted in FIG. 11. In particular, an improved sensor, monitoring and decision support technology is provided for patients who may be prone to such pressure injury, including technologies for preventive and rehabilitation medicine and physical therapy pertaining to skin and soft tissue integrity and the avoidance and healing of pressure injury. In some aspects, the physical activity of a patient, whose weight is supported by a support surface, may be measured in order to automatically ascertain whether the activity, or patterns of the activity, exhibit sufficient frequency and variability such as confer certain health benefits or certain health risks, such as development of pressure ulcers in the load-bearing skin and soft tissues. Where the activity or the patterns do manifest such features associated with benefits or risks, then some embodiments described herein may adaptively provide notification to the patient or caregiver. For example, a reminder or other notification may be generated, which comprises one or more notifications emitted at irregular within-day intervals, and which are likely to establish, restore, or sustain healthy patterns of movement and pressure-relief from the load-bearing tissues in contact with the support surface.

Accordingly, measurements of pressure associated with mechanical loading of a support surface by suprajacent body parts of a person may be used to determine patterns of load-bearing and moment-to-moment adjustments of position. In some embodiments, measurements may be determined using a specialized sensor apparatus associated with a support surface, such as described in connection with measurement device 141 of FIG. 1A and FIGS. 3A-3C. The measurements may be received continuously, periodically, at intervals, or as needed.

In an embodiment, a time series of these measurements are determined and used to determine frequency power spectra for a set of time-periods. In some embodiments, the set of time-periods may comprise consecutive or substantially consecutive time intervals. For instance, in one embodiment, the consecutive time-periods are approximately between 15 and 30 minutes. Other time intervals are also contemplated; such time intervals may be sufficiently long so that, if movements are inadequate to relieve focal pressure within tissues supporting the load exceeding the closing pressure for small blood vessels within the tissues, ischemia and/or ischemia-reperfusion injury are likely to develop. Chronic, frequently repeated or unremitting episodes of such ischemic exposures are causally related to injury and non-healing of the load-bearing tissue structure.

For a first time-period in the set, such as the current time-period or the most recent time-period, a multi-taper filtered power spectral density is determined over a select frequency band. In some embodiments, the power spectrum for these frequencies then may be normalized. In an embodiment, the frequency band is between 0.001 Hz and 0.03 Hz, and in an embodiment, spectrum frequency values below 0.001 Hz and above 0.10 Hz are discarded. In an embodiment, where normalization is performed, the calculated power spectrum at the remaining frequencies of the selected band may be normalized to the power spectral density at 0.001 Hz, such as by setting the value at 0.001 Hz to be equal to 1.0. The resulting pressure power spectrum for the first time-period may transformed as a log-log matrix. For instance, in an embodiment it may be transformed with spectral density in dB for each value of log 10(frequency).

Figure 5A:
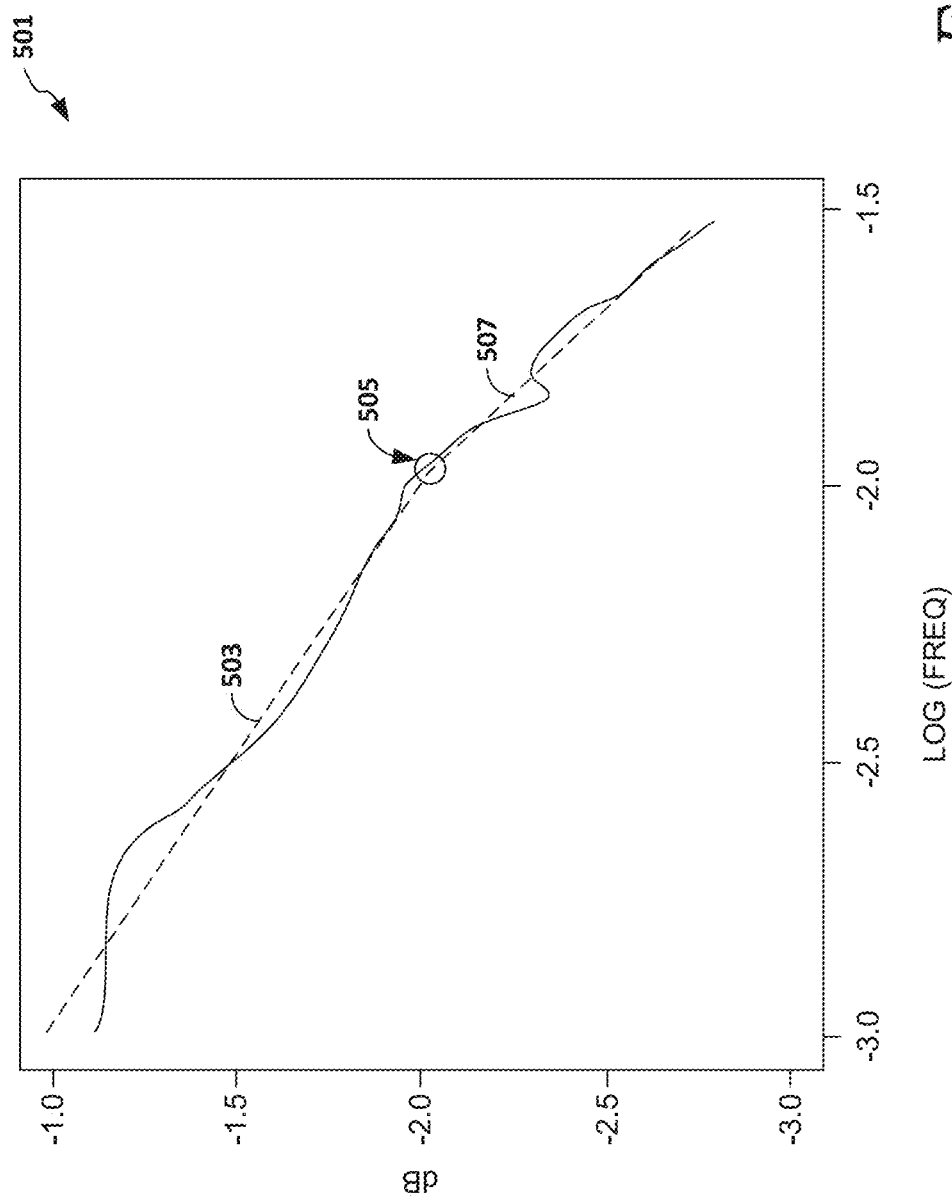
FIGS. 5A-5C depict examples of time series pressure spectra derived from pressure measurements for a patient having normal (healthy) movement on a pressure measurement device, determined in accordance with an embodiment of the disclosure.
Figure 5B:
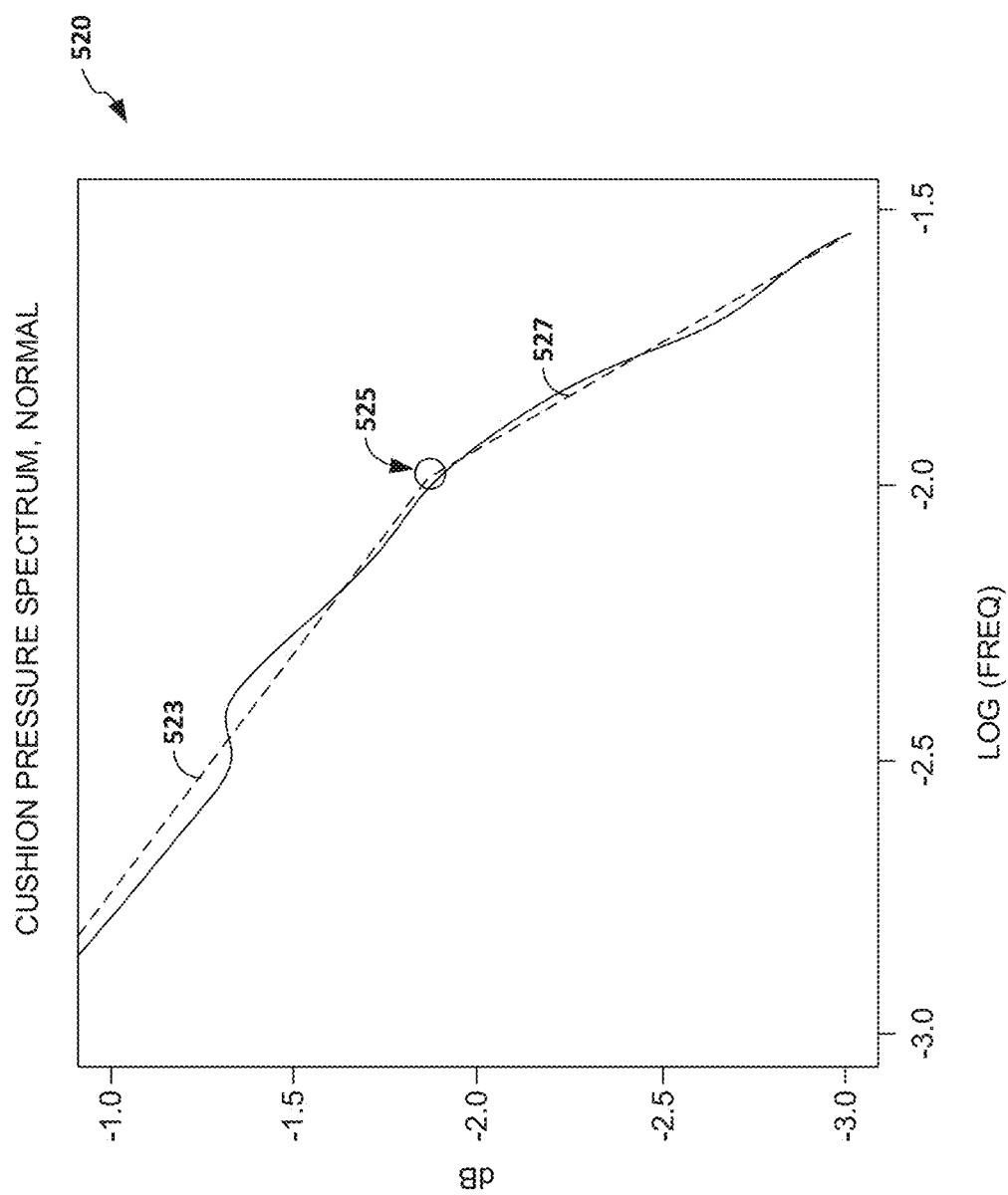
Figure 5C:
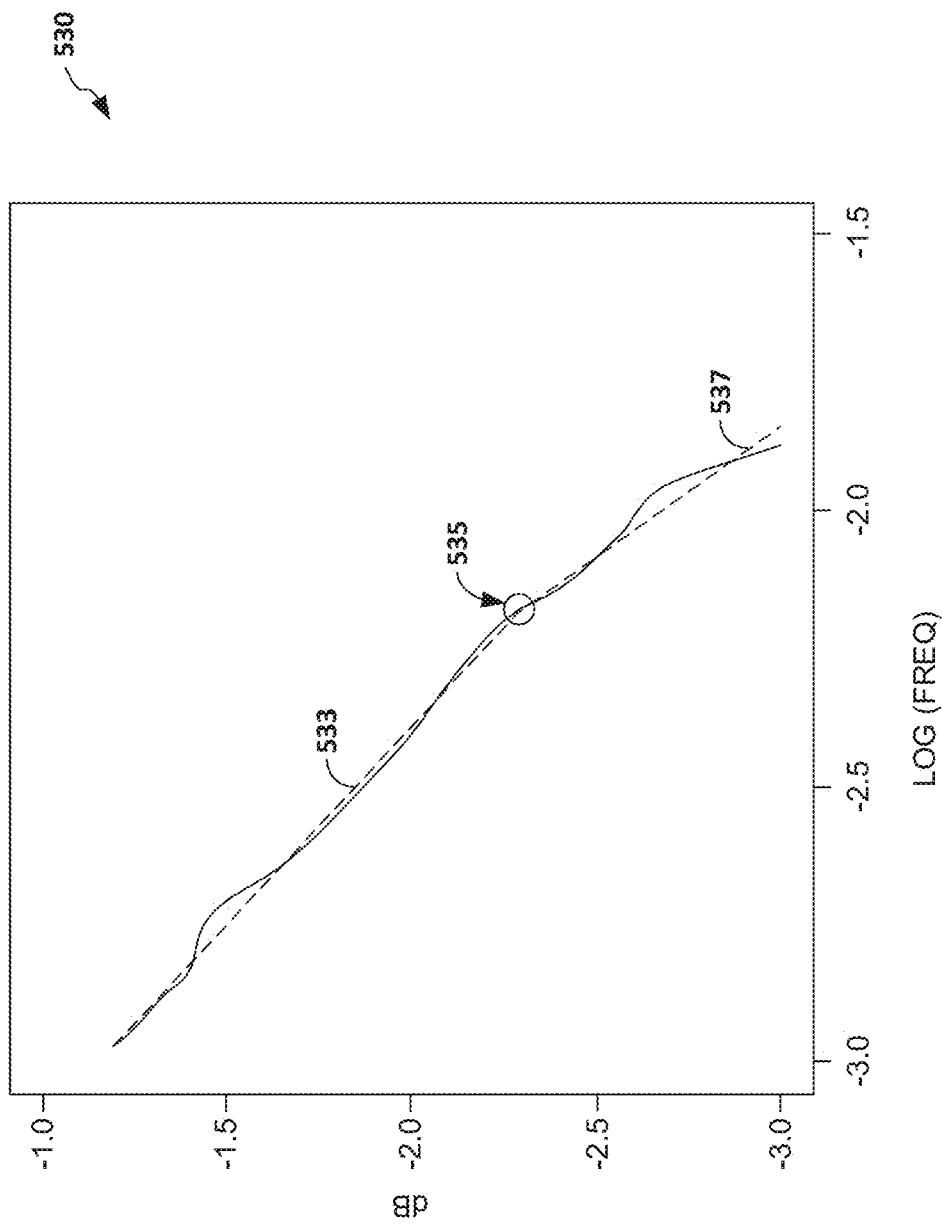
Figure 5D:
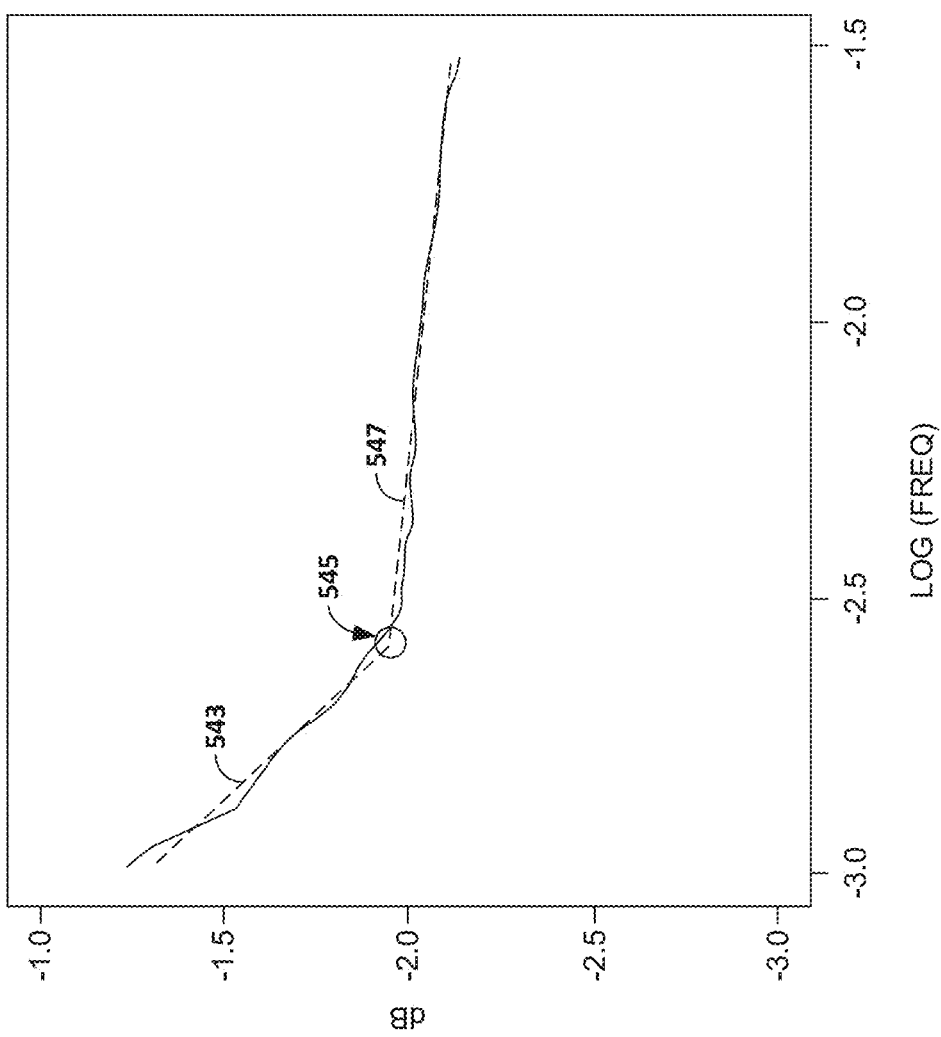
FIGS. 5D-5F depict examples of time series pressure spectra derived from pressure measurements for a patient having movement likely to result in pressure ulcers, determined in accordance with an embodiment of the disclosure.
Figure 5E:
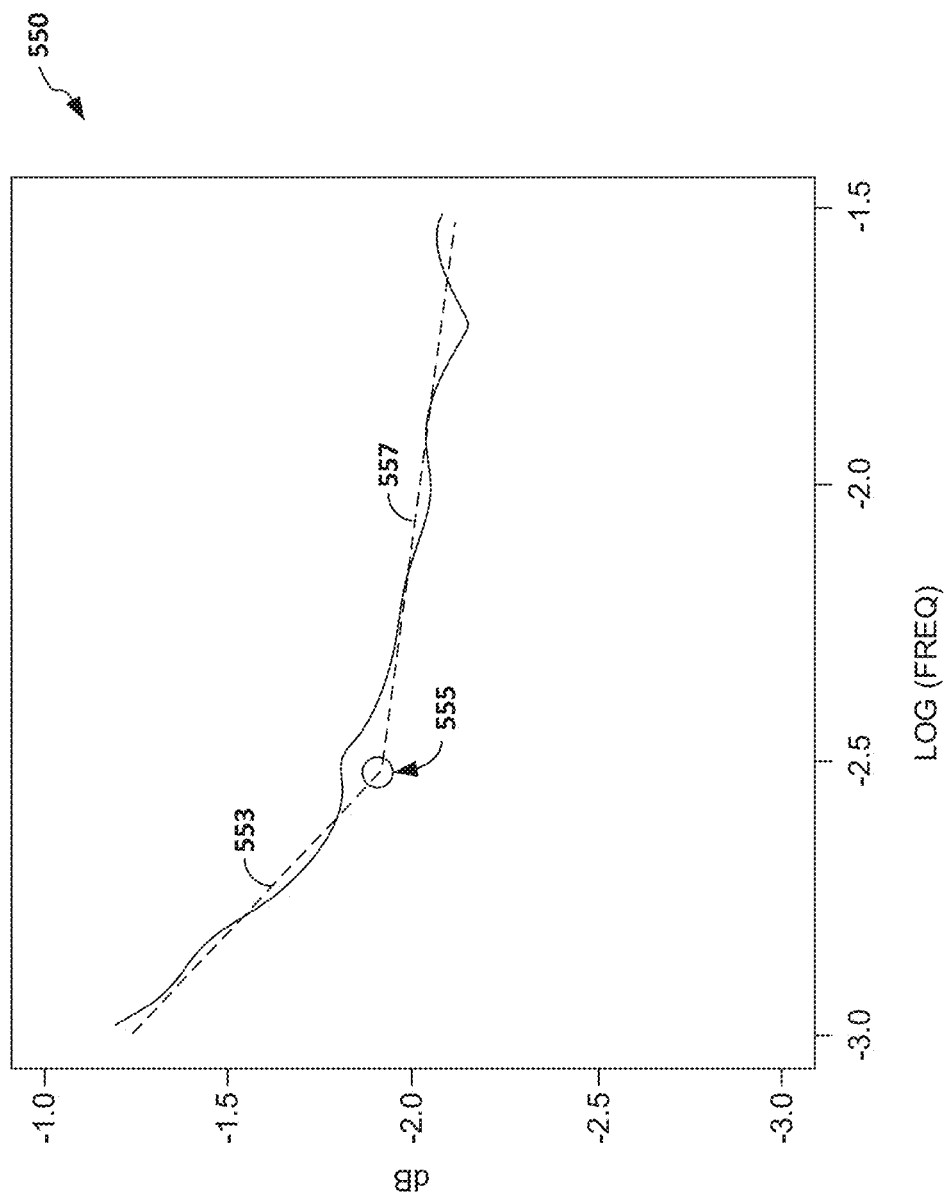
Figure 5F:
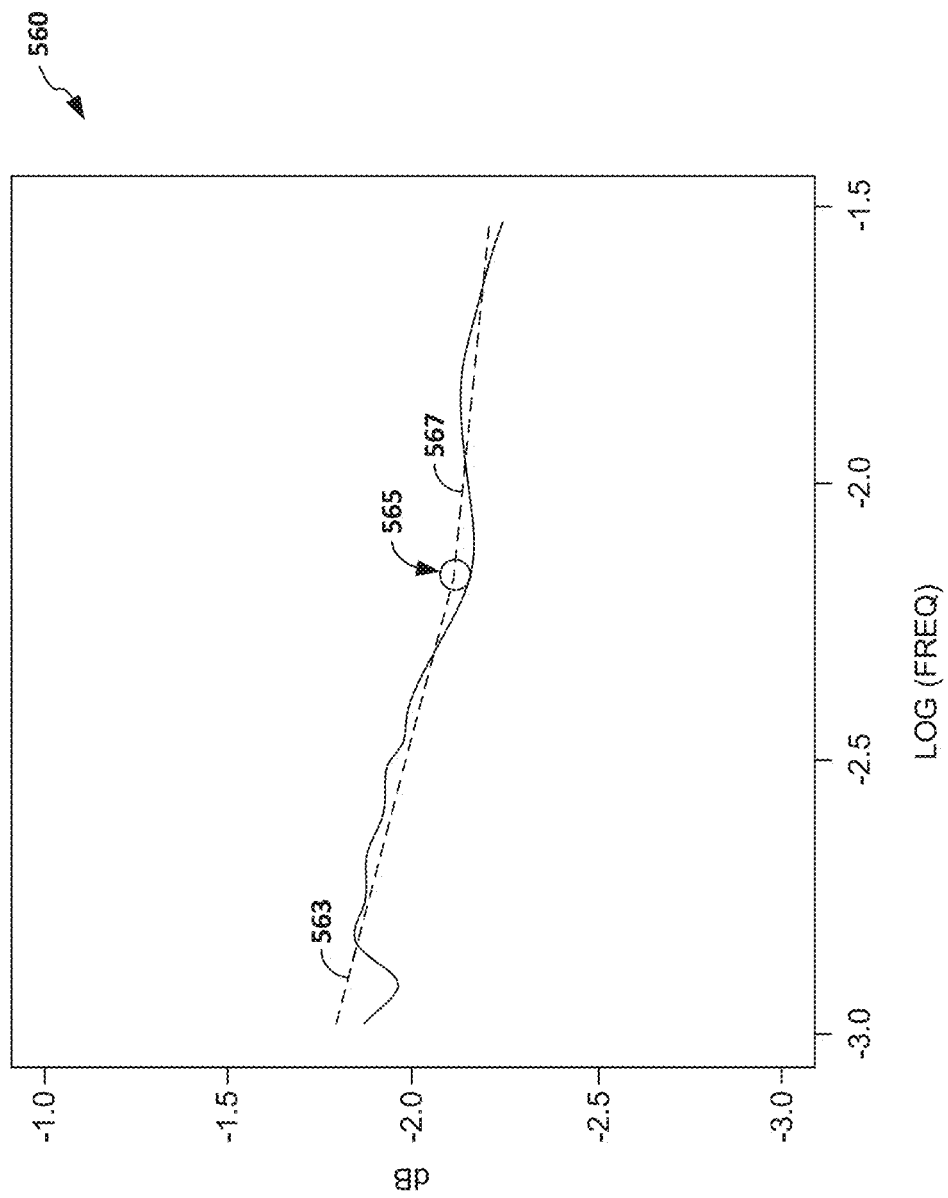
Figure 6A:
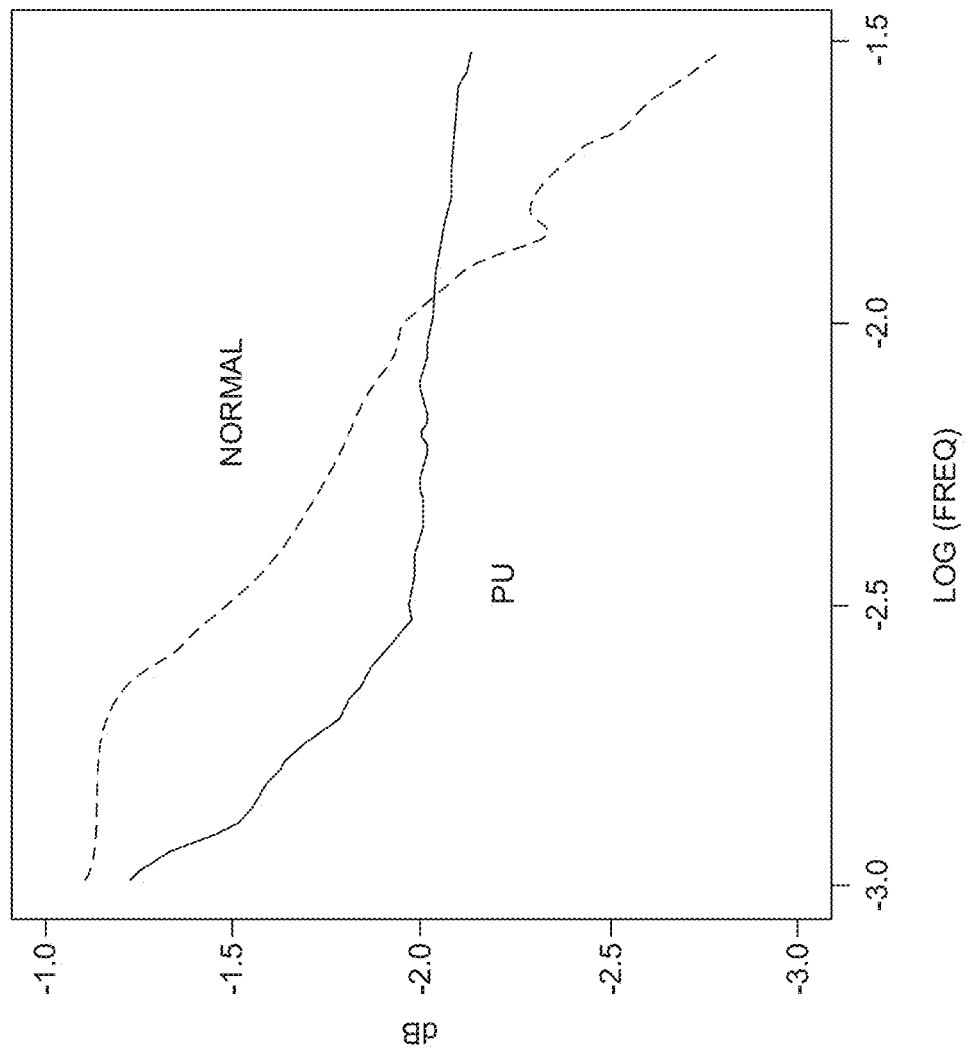
FIGS. 6A-6C depict example comparisons of time series pressure spectra derived from pressure measurements for a patient having healthy movement vs. a patient having movement likely to result in pressure ulcers, determined in accordance with an embodiment of the disclosure.
Figure 6B:
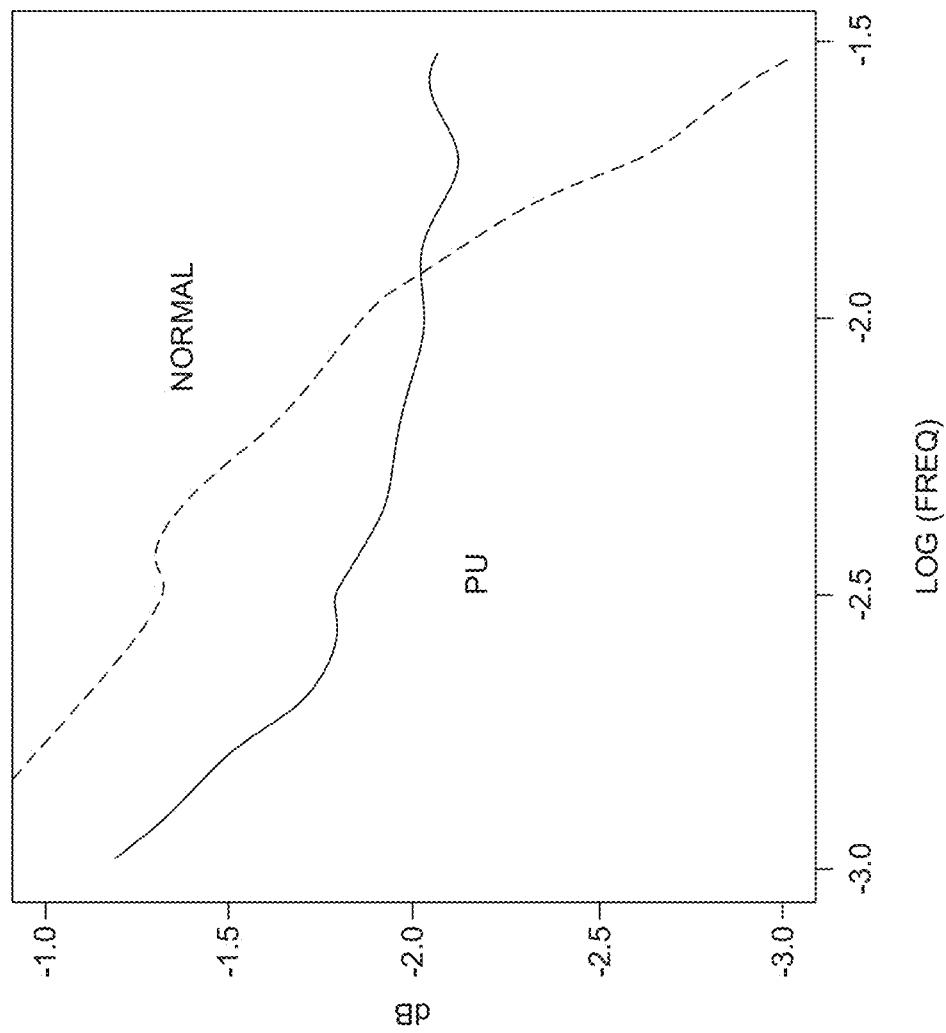
Figure 6C:
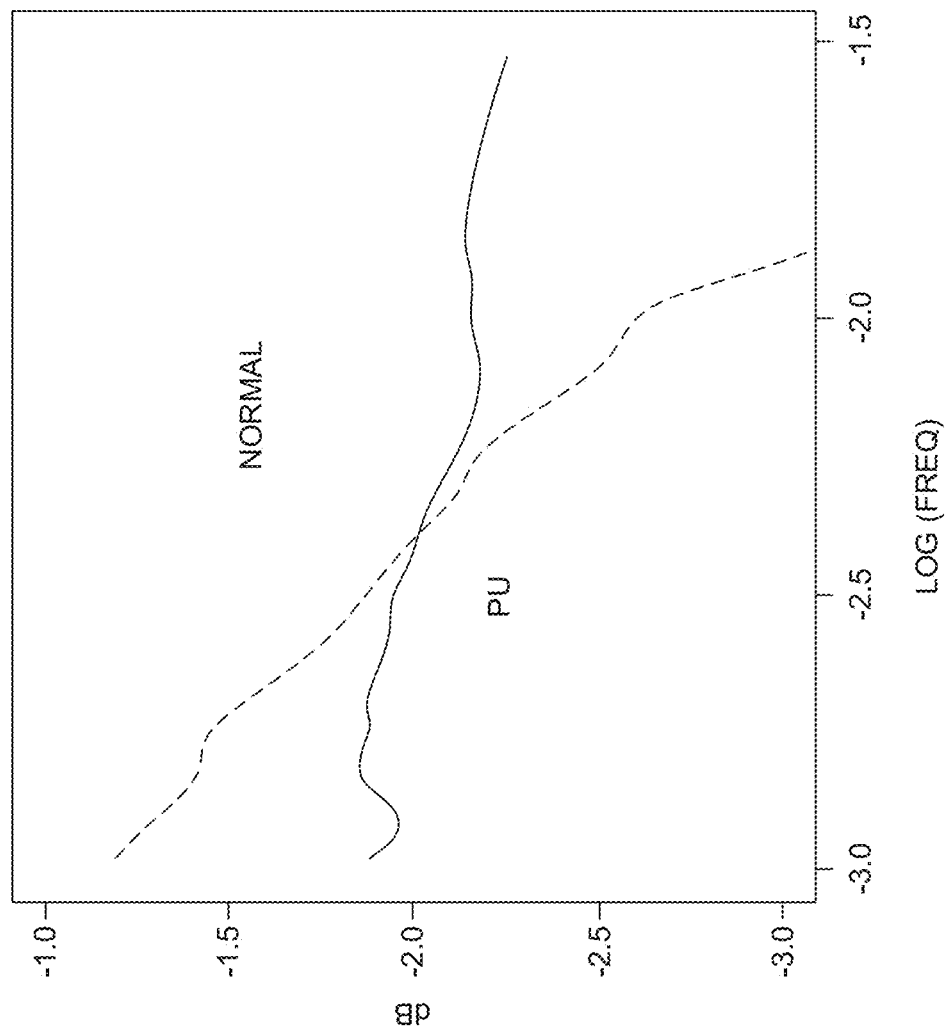

A segmented linear regression of this log-transformed power spectra then may be computed and an optimal cut-point may be determined separating the line-segments. In an embodiment, linear regression is calculated for two piecewise line-segments, and may be in a frequency band between 0.001 Hz and 0.1 Hz. For example, FIGS. 5A-5C (corresponding to normal movement) and FIGS. 5D-5F (corresponding to movement likely to cause or worsen pressure injury) depict instances of two piecewise line-segments with an optimal cut-point (e.g., segments 503 and 507, and cut-point 505 shown in FIG. 5A). In an embodiment, least-squares or a similar method is utilized, and in an embodiment, the R-system package "segmented" may be used to facilitate this calculation and determination.

Figure 4:
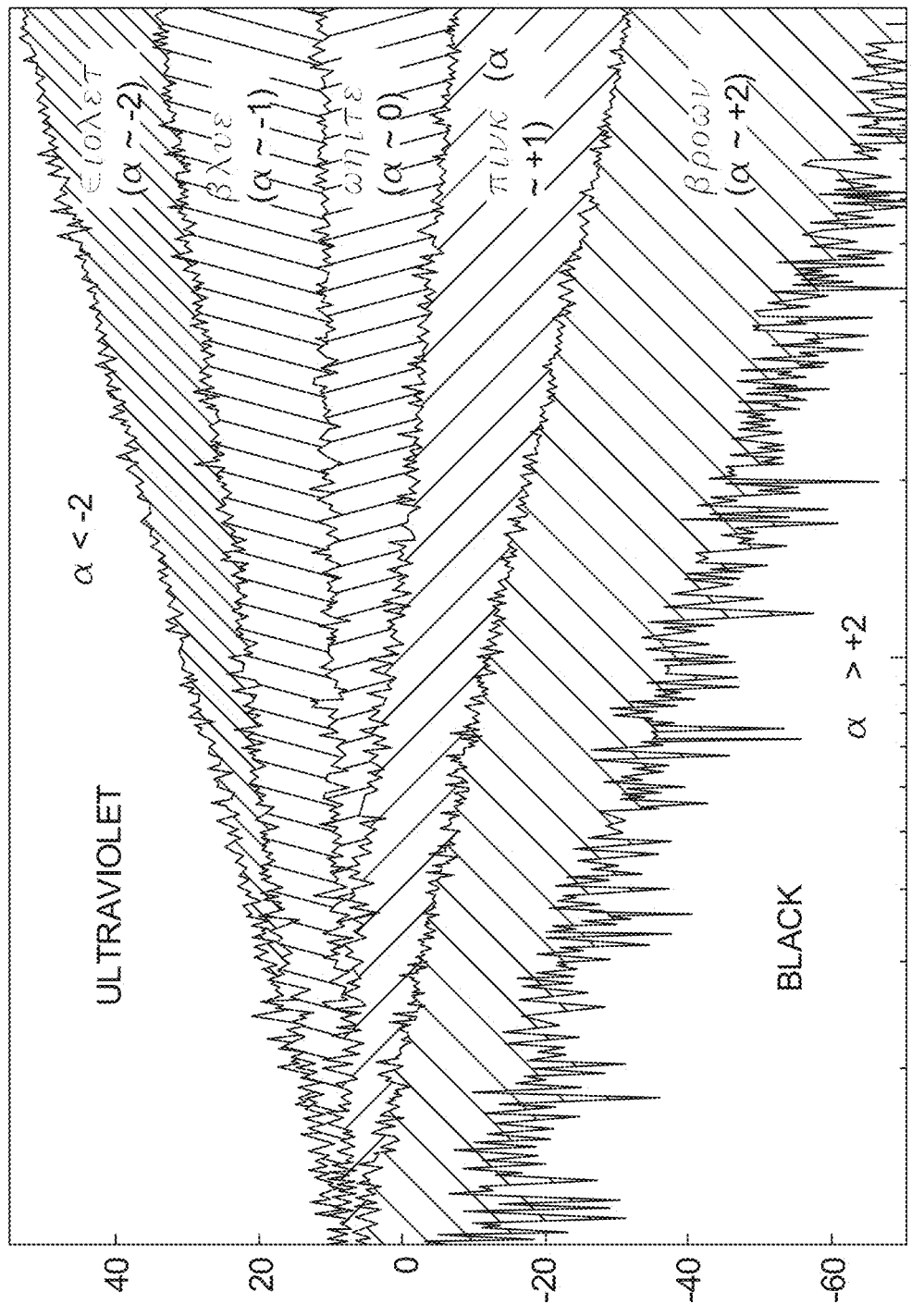
FIG. 4 depicts the colors of noise for power spectral densities as a function of frequency.

The first-order (slope) coefficient for the segments' linear regressions are then compared to characteristic white-, pink-, brown-, and black-noise α values for $1/f^\alpha$ power roll-off. In an embodiment, $\alpha \in (-0.6,+0.4]$, $\alpha \in (+0.4,+1.4]$, $\alpha \in (+1.4,+2.0]$, and $\alpha > +2.0$, respectively), such as shown in FIG. 4. Based on this comparison, it may be inferred that the time-period has conditions for forming pressure-ulcers. In particular, in one embodiment, if the slope coefficient in the frequency band between 0.003 Hz and 0.10 Hz matches a $1/f^\alpha$ power roll-off of $\alpha \in (-0.6,+0.41]$, then it is determined that the condition for the time period associated with this power spectrum is pressure ulcer-prone. Accordingly, such embodiments function as a sensor (e.g., a smart sensor) by more accurately detecting, using the algorithm described above and including the comparison, those dangerous conditions which may promote ulcer formation (or impede healing). Similarly, these embodiments more accurately detect healthy conditions unlikely to promote ulcer formation.

Next, according to some embodiments, the linear regression coefficients for previous (or prior) time-periods' determine pressure spectra are received. A duty-cycle may be determined of patterns whose frequency spectra are associated with pressure ulcer proneness. In particular, a duty-cycle of high-frequency pressure-ulcer-prone white-noise spectrum condition among the first (or current) time-period's regression values and the N−1 previous time-period's regression values. For example, the duty cycle may be determined as a daily cumulative percentage of time. In an embodiment, a duty-cycle of N periods (N−1 precious time periods and the current or a recent time period, N) is determined of high-frequency white noise spectrum (indicating pressure-ulcer-prone conditions) in a frequency band between 0.003 and 0.1 Hz. Where the duty cycle of the high-frequency pressure-ulcer-prone white-noise spectrum condition exceeds a threshold value, then it may be inferred that tissue breakdown occurs and pressure ulcers are likely to form. Similarly, if pressure ulcers are already present in the affected skin and soft tissue, the pressure ulcers are unlikely to heal. The threshold may be pre-determined, determined by a clinician, or determined based on a condition of the patient. For instance, a patient that is determined to be more prone to pressure injury (or a patient already having pressure injury) may have a lower threshold. Similarly a heavier patient may have a lower threshold than a lighter patient. In an embodiment, a threshold of duty-cycle of fifty percent is utilized.

In one embodiment, a notification may be provided or another intervening action may be invoked. For instance, one intervening action comprises generating a notification that may be emitted or otherwise communicated to the patient or to a caregiver, such as a provider clinician responsible for the care of the patient. For example, an electronic advisory or warning message may be emitted to a human user, such as a caregiver, indicating an elevated risk of pressure injury to the user, to encourage the user to initiate more frequent movements of position with respect to the load-bearing support surface. In an embodiment, the action comprises generating and emitting or communicating the notification, which may be emitted/communicated via a bedside or patient-side alarm, user/clinician interface (such as interface 142 described in FIG. 1A), or may be communicated to a smartphone or personal computing device of a caregiver, thereby alerting them of an impending deterioration of the patient's condition. In one embodiment, the notification comprises an event signal and includes the likelihood of future pressure injury to the user. In some embodiments, the intervening action comprises adaptively providing notification at irregular within-day intervals. In particular, the irregular intervals may be more likely—verses regularly or predictably provided alerts—to provoke a positive response to establish, restore, or sustain healthy patterns of movement and pressure-relief from the load-bearing tissues in contact with the support surface.

Another action that may be initiated, based on the determined likelihood, comprises a recommendation for modifying a care plan or treatment procedure associated with the patient; for example, a recommendation may comprise one or more movements or activity to be performed by the patient or by a caregiver to the patient, increasing patient monitoring or level of care, operating on the patient, or administering another similarly effective therapeutic intervention. The recommendation may be provided in conjunction with a notification, and/or may be provided via a user/clinician interface, such as interface 142, described in connection with FIG. 1A.

Yet another action that may be initiated, based on the determined likelihood, comprises automatically modifying computer code executed in a healthcare software program for treating the patient, thereby transforming the program at runtime. For example in one embodiment, the modification comprises modifying (or generating new) computer instructions to be executed at runtime in the program, the modification may correspond to a change in a care plan, treatment procedure, or therapeutic intervention to be administered to the patient due to the determined likelihood of pressure injury occurrence. In one instance, the modification comprises changing the executed computer instructions corresponding to monitoring the patient's condition, such as increasing the frequency of obtaining physiological measurements of the patient, or increasing sensitivity of monitoring physiological changes in a patient.

Yet another action that may be initiated, based on the determined likelihood, comprises scheduling healthcare resources for the patient. For example in one embodiment, a physical therapy resource may be automatically reserved for the patient, healthcare staff may be notified and/or automatically scheduled, or transportation/support staff or resources for getting the patient to a healthcare facility may be called. In one embodiment, this action comprises modifying or updating a resource/scheduling electronic record in a resource/scheduling system, such as operated as part of a hospital or healthcare system. In one embodiment, the action comprises, upon a sufficient determined likelihood of a future pressure injury or event occurrence (wherein significance may be determined using a threshold, as described in method 200 of FIG. 2), initiating a computer instruction that modifies the scheduling healthcare resources, which may include computer instructions for automatically alerting, scheduling, and/or notifying staff, reserving rooms, transportation, or other equipment/space, and which may include changing the priority of the patient (when compared to other patients) for receiving these resources.

As described previously, embodiments of this disclosure provide improved methods and systems for reducing pressure injury. A number of problems exist in the conventional approaches and technologies to monitoring and reducing such injuries. For example, measurement and analytics methods, such as thermal imaging or pressure heat-mapping devices, address only weekly or other longer timescale patterns, and do not address ultradian (short timescale) patterns' relationship to the likelihood of ischemia in skin and soft tissues, ischemia-reperfusion injury, necrosis, and development of pressure ulcers. These conventional measurement technologies are often only determined one time, such as a diagnostic method. It is not practical or effective to utilize these technologies in repeated or ongoing assessments of evolving risk or time-dependent load-bearing patterns and pressure exposures in the course of routine daily activities. Additionally, the underlying measurement apparatus for these technologies is expensive, and may further require expert configuration or setup, and therefore is not financially practical for routine or ongoing use in home or other ambulatory locations. Further, these apparatus are complex and not suitable for operation by individuals who have certain physical disabilities or by their caregivers.

Further still, the conventional technologies lack adequate statistical sensitivity to detect conditions that give rise to pressure injury of skin and soft tissues and, therefore, suffer from excessively high false-negative determinations, giving false reassurance regarding individuals who do go on to develop pressure ulcers or fail to heal existing pressure ulcers. Moreover, many of these conventional technologies have inadequate statistical specificity to rule-out conditions that give rise to pressure injury of skin and soft tissues and to determine safe conditions that avoid injury and, therefore, suffer from excessively high false-positive determinations of pressure injury risk in individuals who are not in fact at-risk of such injury. These and other deficiencies and limitations are mitigated or overcome by the technologies described herein. Many of these embodiments are also not susceptible to biases, and are tolerant of modest amounts of missing or sensing-artifact contaminated values of model-variables information. Additionally, many embodiment of the present disclosure provide additional advantages of not requiring extensive configuration or intrusive questioning or detailed self-reporting of information from patients.

Figure 1A:
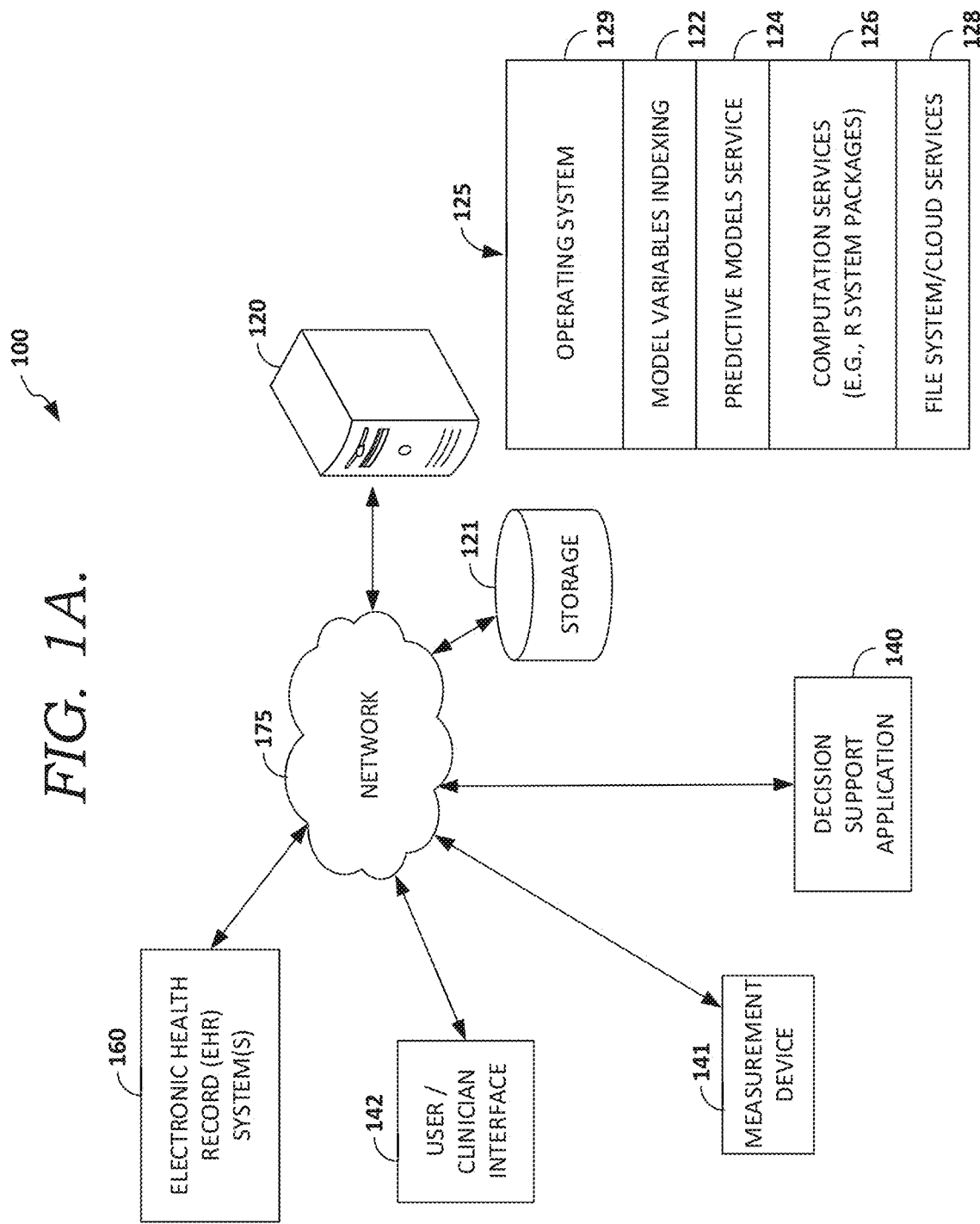
FIGS. 1A and 1B depict aspects of an illustrative operating environment suitable for practicing an embodiment of the disclosure.

Referring now to the drawings in general, and initially to FIG. 1A in particular, an aspect of an operating environment 100 is provided suitable for practicing an embodiment of the technologies described herein. We show certain items in block-diagram form more for being able to reference something consistent with the nature of a patent specification than to imply that a certain component is or is not part of a certain device. Similarly, although some items are depicted in the singular form, plural items are contemplated as well (e.g., what is shown as one data store might really be multiple data-stores distributed across multiple locations). But showing every variation of each item might obscure the invention. Thus for readability, we show and reference items in the singular (while fully contemplating, where applicable, the plural).

As shown in FIG. 1, a block diagram is provided showing aspects of an example computing system architecture suitable for implementing an embodiment of this disclosure and designated generally as example operating environment 100. Example operating environment 100 provides an aspect of a computerized system for compiling and/or running aspects of this disclosure including monitoring, detecting or determining, and/or predicting a likely future occurrence (or event) of a pressure injury or conditions prone to induce such injury, and additional decision support technology to facilitate caring for patients who may be prone to experience these injuries.

Operating environment 100 is one example of a suitable environment and system architecture for implementing an embodiment of the disclosure. Other arrangements and elements can be used in addition to or instead of those shown, and some elements may be omitted altogether for the sake of clarity. Further, as with operating environment 100, many of the elements described herein are functional entities that may be implemented as discrete or distributed components or in conjunction with other components, and in any suitable combination and location. As described above, some embodiments may be implemented as a system, comprising one or more computers and associated network and equipment, upon which a method or computer software application is executed. Accordingly, aspects of the present disclosure may take the form of an embodiment combining software and hardware aspects that may all generally be referred to herein as a "module" or "system." Further, the methods of the present disclosure may take the form of a computer application embodied in computer readable media having machine-readable application software embodied thereon. In this regard, a machine-readable storage media may be any tangible medium that can contain, or store a software application for use by the computing apparatus.

Computer application software for carrying out operations for system components or steps of the methods of the present disclosure may be authored in any combination of one or more programming languages, including an object-oriented programming language such as Java, Python, R, or C++ or the like. Alternatively, the application software may be authored in any or a combination of traditional non-object-oriented languages such as C or Fortran. The application may execute entirely on the user's computer (i.e., a computing device) as an independent software package, or partly on the user's computer in concert with other connected co-located computers or servers, or partly on the user's computer and partly on one or more remote computers, or entirely on a remote computer or collection of computers. In the latter cases, the remote computers may be connected to the user's computer through any type of network, including a local area network (LAN) or a wide area network (WAN), or the connection may be made to an external computer (for example, via the internet using an Internet Service Provider or ISP) or an arbitrary, geographically-distributed, federated system of computers, such as a cloud-based system.

Moreover, the components of operating environment 100, functions performed by these components, or services carried out by these components may be implemented at appropriate abstraction layer(s) such as the operating system layer, application layer, hardware layer, etc., of the computing system(s). Alternatively, or in addition, the functionality of these components and/or the embodiments described herein can be performed, at least in part, by one or more hardware logic components. For example, and without limitation, illustrative types of hardware logic components that can be used include Field-programmable Gate Arrays (FPGAs), Application-specific Integrated Circuits (ASICs), Application-specific Standard Products (ASSPs), System-on-a-chip systems (SOCs), Complex Programmable Logic Devices (CPLDs), etc. Additionally, although functionality is described herein with regards to specific components shown in example operating environment 100, it is contemplated that in some embodiments functionality of these components can be shared or distributed across other components.

Environment 100 includes one or more electronic health record (EHR) systems, such as EHR system(s) 160 communicatively coupled to network 175, which is communicatively coupled to computer system 120. In some embodiments, components of environment 100 that are shown as distinct components may be embodied as part of or within other components of environment 100. For example, EHR system(s) 160 may comprise one or a plurality of EHR systems such as hospital EHR systems, health information exchange EHR systems, clinical genetics/genomics systems, ambulatory clinic EHR systems, psychiatry/neurology EHR systems, insurance, collections or claims records systems; and may be implemented in or as a part of computer system 120. Similarly, EHR system(s) 160 may perform functions for two or more of types of EHR systems (not shown). EHR system(s) 160 also may include records of physiological variables (such as vital signs measurements) obtained via one or more measurement apparatus, tests, or screenings, such as measurement device 141.

In some embodiments of the technologies described herein, aspects of a decision support tool for patients having or at risk for developing a pressure injury condition or event occurrence or recurrence may utilize data about a population of patients derived from patient EHR or other records information. In particular, presently certain data warehouses are created for purposes of public health and observational research purposes and are derived from electronic health records repositories in such a way that they are de-identified so as to comply with applicable confidentiality laws and regulations. The Cerner Health Facts™ data warehouse is such a system that has been curated for more than 15 years. It comprises a large 'transaction database' where each entry corresponds to a patient's 'basket' (a collection of items recorded or transacted at points in time during episodes of care services provisioning in the contributing health care institutions). Each database entry is ordered by the date-time of the transaction. Transaction sequencing is implemented by grouping medical events occurring in the same 'epoch' for the same patient together into 'baskets' and ordering the 'baskets' of each patient by the date-time stamps where the events occurred. Epoch durations may differ according to the age of the patient, or the acute or chronic nature of the health conditions that pertain to the patient, or the rate of change of the severity of the health conditions, or other factors, Epoch durations may be as short as a few minutes (as in critical care ICU or operating room contexts) or may be as long as 10 years or more (as in chronic ambulatory care-sensitive conditions, ACSCs).

Continuing with FIG. 1A, network 175 may comprise the Internet, and/or one or more public networks, private networks, other communications networks such as a cellular network, or similar network(s) for facilitating communication among devices connected through the network. In some embodiments, network 175 may be determined based on factors such as the source and destination of the information communicated over network 175, the path between the source and destination, or the nature of the information. For example, intra-organization or internal communication may use a private network or virtual private network (VPN). Moreover, in some embodiments items shown communicatively coupled to network 175 may be directly communicatively coupled to other items shown communicatively coupled to network 175.

In some embodiments, operating environment 100 may include a firewall (not shown) between a first component and network 175. In such embodiments, the firewall may reside on a second component located between the first component and network 175, such as on a server (not shown), or reside on another component within network 175, or may reside on or as part of the first component.

Embodiments of electronic health record (EHR) system(s) 160 include one or more data stores of health-related records, which may be stored on storage 121, and may further include one or more computers or servers that facilitate the storing and retrieval of the health records. In some embodiments, EHR system(s) 160 and/or other records systems may be implemented as a cloud-based platform or may be distributed across multiple physical locations. EHR system(s) 160 may further include record systems, which store real-time or near real-time patient (or user) information, such as wearable sensor or monitor, support-surface, bedside, laboratory, or in-home patient monitors or sensors, for example, such as measurement device 141.

Example operating environment 100 further includes a user/clinician interface 142 and decision support application 140, each communicatively coupled through network 175 to an EHR system 160. Although environment 100 depicts an indirect communicative coupling between interface 142 and application 140 with EHR system 160 through network 175, it is contemplated that an embodiment of interface 142 or application 140 are communicatively coupled to EHR system(s) 160 directly. For example, in one embodiment a decision support application 140 operating at least in part on a client device (such as a user-operated computer device like a tablet) includes an interface 142 (which may comprise a graphical user interface), which may be used for accessing patient information from an EHR system(s) 160.

An embodiment of decision support application 140 comprises a software application or set of applications (which may include programs, routines, functions, or computer-performed services) residing on a client computing device (or distributed in the cloud and on a client computing device) such as a personal computer, laptop, smartphone, tablet, or mobile computing device. In an embodiment, the application is a Web-based application or applet, and may be used to provide or manage user services provided by an embodiment of the technologies described herein, which may be used by a caregiver or screener to provide, for example, information about the likelihood of a specific patient or population of patients to have or develop an acute inflammatory condition or event, which may occur at a future time, and may further include a degree or level characterizing the severity of the condition or event. In some embodiments, application 140 includes or is incorporated into a computerized decision support tool, as described herein. Further, some embodiments of application 140 utilize user/clinician interface 142.

In some embodiments, application 140 and/or interface 142 facilitates accessing and receiving information from a user or health care provider about a specific patient or set of patients, according to the embodiments presented herein. Embodiments of application 140 also may facilitate accessing and receiving information from a user or health care provider about a specific patient, caregiver, or population including historical data; health care resource data; physiological variables or other patient-related measurements, time series, and predictions (including plotting or displaying the determined outcome and/or issuing an alert) described herein; or other health-related information, and facilitates the display of results, recommendations, or orders, for example. In an embodiment, application 140 also facilitates determining, receiving, or providing: notifications, recommendations, care plan changes, or orders, staffing scheduling, and/or queries from a user, which may be based on the results of monitoring and/or forecasted outputs, and which may in some embodiments utilize user interface 142. Decision-Support application 140 may also be used for providing diagnostic services or evaluation of the performance of various embodiments.

In some embodiments, user/clinician interface 142 may be used with application 140, such as described above. One embodiment of user/clinician interface 142 comprises a user interface that may be used to facilitate access by a user (including a clinician/caregiver such as a medical caregiver, physical therapist, or the like) to a probability, likelihood, forecast, score or prediction determined according to the technologies described herein, including information indicating a likelihood that a patient is experiencing conditions likely to cause or exacerbate pressure injury or will experience such as condition or event, or other aspects described herein. One embodiment of interface 142 takes the form of a graphical user interface and application, which may be embodied as a software application (e.g., decision support application 140) operating on one or more mobile computing devices, tablets, smartphones, front-end terminals in communication with back-end computing systems, laptops, or other computing devices. In an embodiment, the application includes the PowerChart® software manufactured by Cerner Corporation. In an embodiment, interface 142 includes a Web-based application (which may take the form of an applet or app) or set of applications usable to manage user services provided by an embodiment of the technologies described herein.

In some embodiments, interface 142 may facilitate providing the output of the determined measurements, forecast(s), probabilities (or score), recommendations, scheduling orders, providing instructions (such as measuring, recording, and/or otherwise obtaining vital signs or other physiological variable measurements), confirmations or notifications (which may include, for example, confirmation that information has been received or notifications that information has not been received and there may be an error in the measuring instrument, user operation of a measurement device, or measurement procedure), reminders (such as notifications to obtain a physiological measurement sample), or outputs of other actions described herein, as well as logging and/or receiving other feedback from the user/caregiver, in some embodiments. In an embodiment, interface 142 also facilitates receiving orders for the patient from the clinician/user, based on the results of monitoring and predictions. Interface 142 also may be used for facilitating diagnostic services or evaluation of the performance of various embodiments.

Example operating environment 100 includes measurement device 141 communicatively coupled through network 175 to an EHR system 160. In an embodiment, measurement device 141 (sometimes referred to herein as a patient-interface component) comprises one or more sensor components operable to acquire clinical or physiological information about a patient, such as various types of physiological measurements, physiological variables, or similar clinical information associated with a particular physical (or mental state) of the patient, and which may be acquired periodically, continuously, as needed, or as they become available, and may be represented as one or more time series of measured variables.

In one embodiment, measurement device 141 comprises one or more sensors configured for obtaining (and in some instances pre-processing or interpreting) pressure-related measurements due to force applied by a patient, which may be static or dynamic as a patient moves. In particular, in some embodiments, measurement device 141 includes a support surface having one or more sensors (which may further comprise or be coupled to a computer system to facilitate storing, pre-processing, processing, transforming the measurements). The pressure-related information may be obtained continuously, periodically, or at irregular intervals. Accordingly, the term measurement is used broadly herein, and it is contemplated that in some embodiments, measurement device 141 may not perform measurement but may receive information about the measured physiological or patient-related parameters (such as pressure caused by the patient being supported on a support surface, and/or other measurements as heart rate (HR), blood pressure (e.g., systolic blood pressure or SBP), respiratory rate (RR), or non-vital variables, for example and without limitation) which may be measured, observed, or otherwise recorded. Some embodiments of measurement device 141 may comprise one or more sensors, an interface component, and/or processing/communications component (not shown), such as wired or wireless telecommunications technologies described herein for communicably coupling sensors with the processors or memory described herein.

Figure 3C:
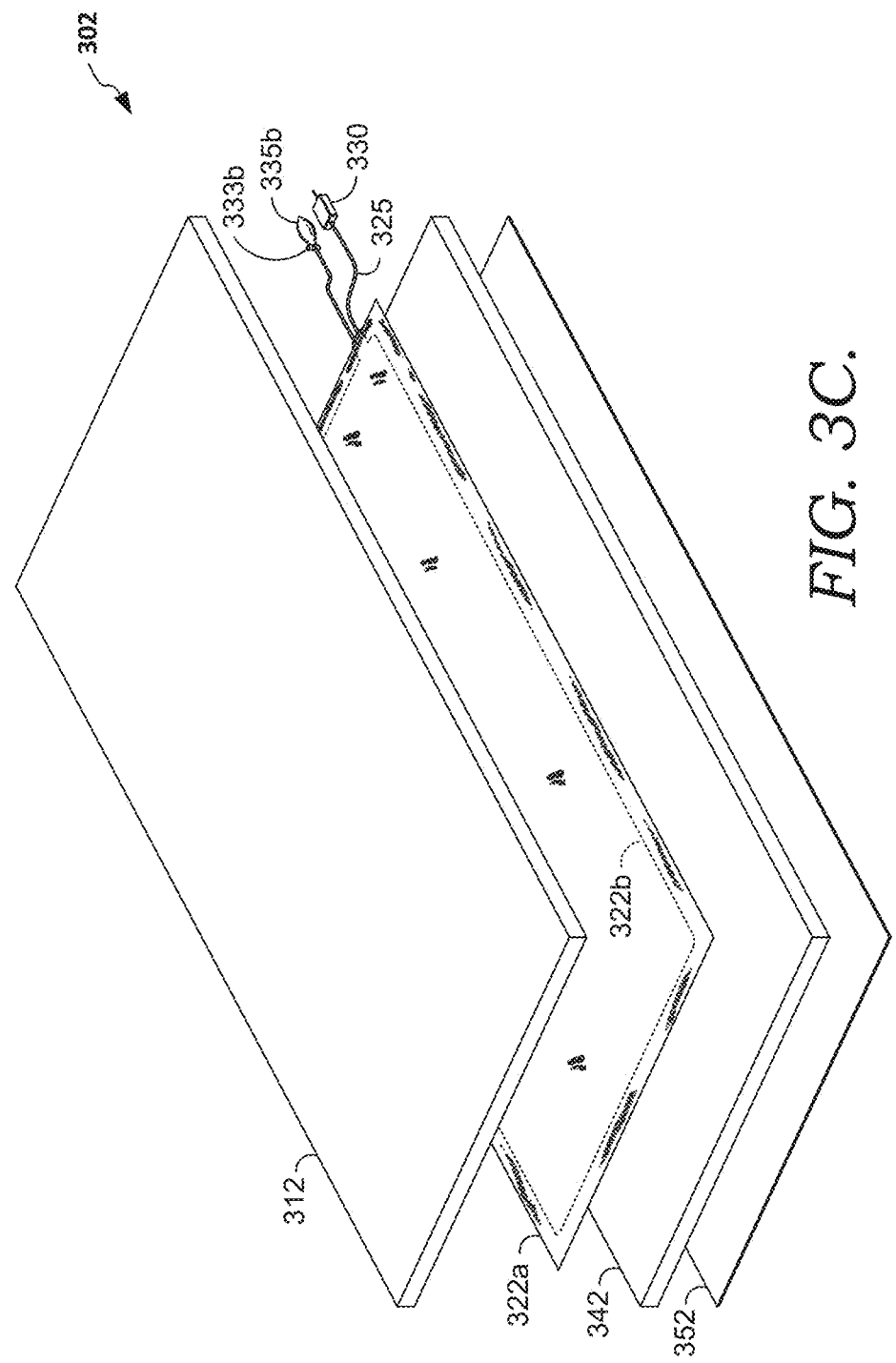

Aspects of one example embodiment of a measurement device 141 are depicted in FIGS. 3A-3G. With reference to FIG. 3A, aspects of an example measurement device 141 are depicted and comprise a multi-layer support surface 300, which in one example may comprise an outer seat-cushion surface 310. In other embodiments, support surface 300 may comprise a mattress-cushion, pad, or other similar support surface for an individual, such as example support surface 302, of FIG. 3C, which is embodied as a mattress. Continuing with FIG. 3A, example support surface 300 further comprises a cushion layer 340 (which may comprise a neoprene foam rubber substrate, similar foam rubber, gel, or a similar compressible but supportive material), cover 350, and air bladder layer 320. Air bladder layer 320 may extend over the entire cross-section of support surface 300 (as shown) or may cover only a portion of the surface, such as the example air bladder 321a and 321b, depicted in support surface 301 of FIG. 3B. In some embodiments, air bladder 320 may comprise one or more air bladders.

Figure 3D:
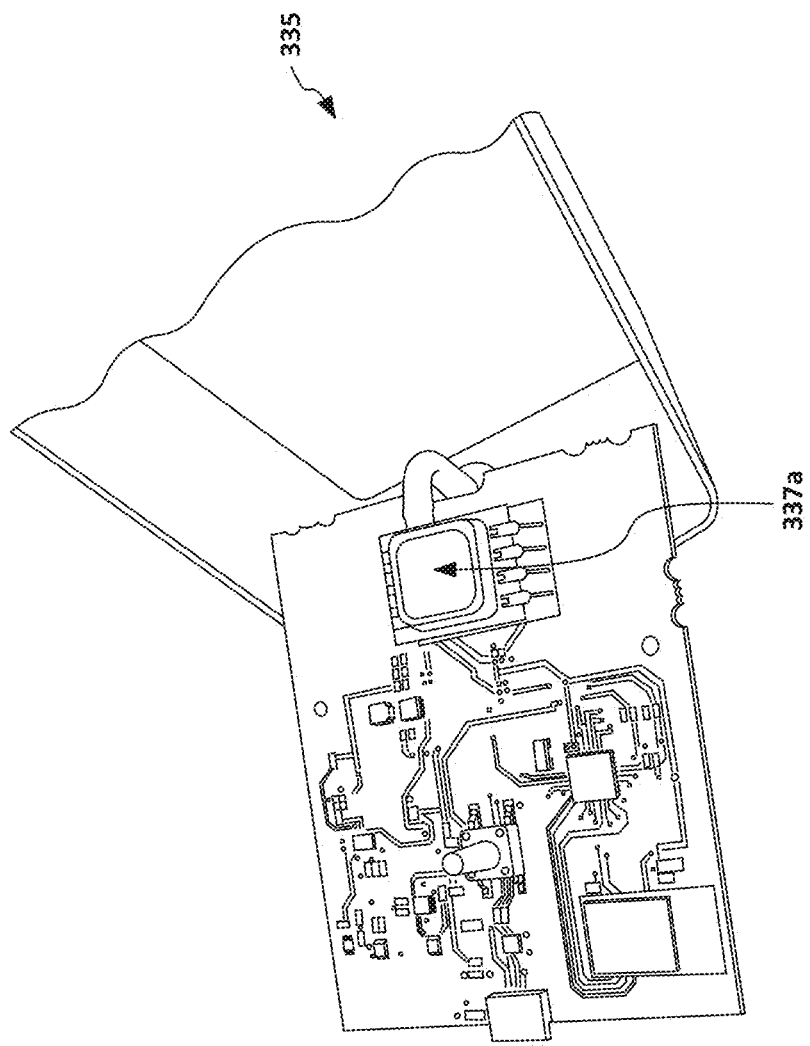
Figure 3E:
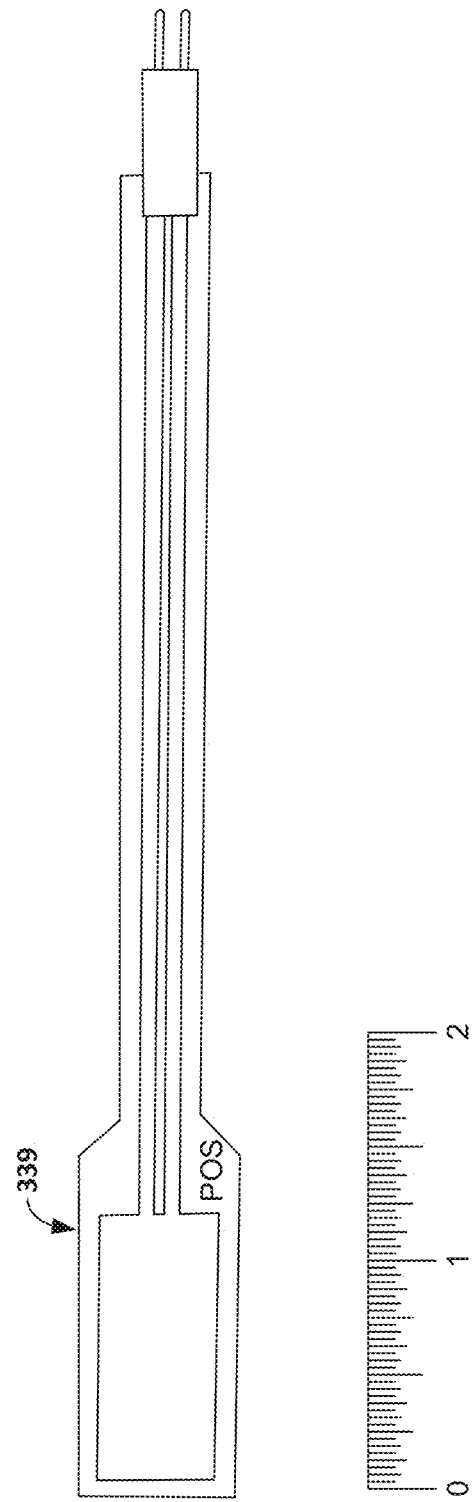

Air bladder 320 is coupled to a pressure sensor(s) component 330. In an embodiment, pressure sensor(s) component comprises one or more sensors (not shown in FIG. 3A), which may include a transducer (such as a force sensing resistor 339, shown in FIG. 3E), which measure pressure determined using air bladder 320. In an embodiment, pressure sensor(s) component 330 comprises a digital pressure sensor, such as the DLV 060A low-voltage digital pressure sensor, manufactured by All Sensors Inc.® of Morgan Hill, California. FIG. 3D depicts an example aspect of an embodiment of pressure sensor(s) component 330 (shown as item 335) with the DLV 060A pressure sensor chip (item 337a of FIG. 3D). In an embodiment, the sensor(s) or component 330 may comprise an ultrasonic-based sensor.

Furthermore, some embodiments of the measurement device 141 may comprise ambient condition sensors (not shown) for providing processors described herein with information regarding ambient conditions proximate to the air bladder 320 and the processors. Using instructions from computer memory associated therewith, the processors may modify the pressure measurements from the pressure sensor component 330 as a function of the information from the ambient condition sensors regarding the ambient conditions of temperature and/or atmospheric pressure so as to compensate for artifacts due to changes in at least one of the ambient temperature and the ambient pressure.

Figure 3G:
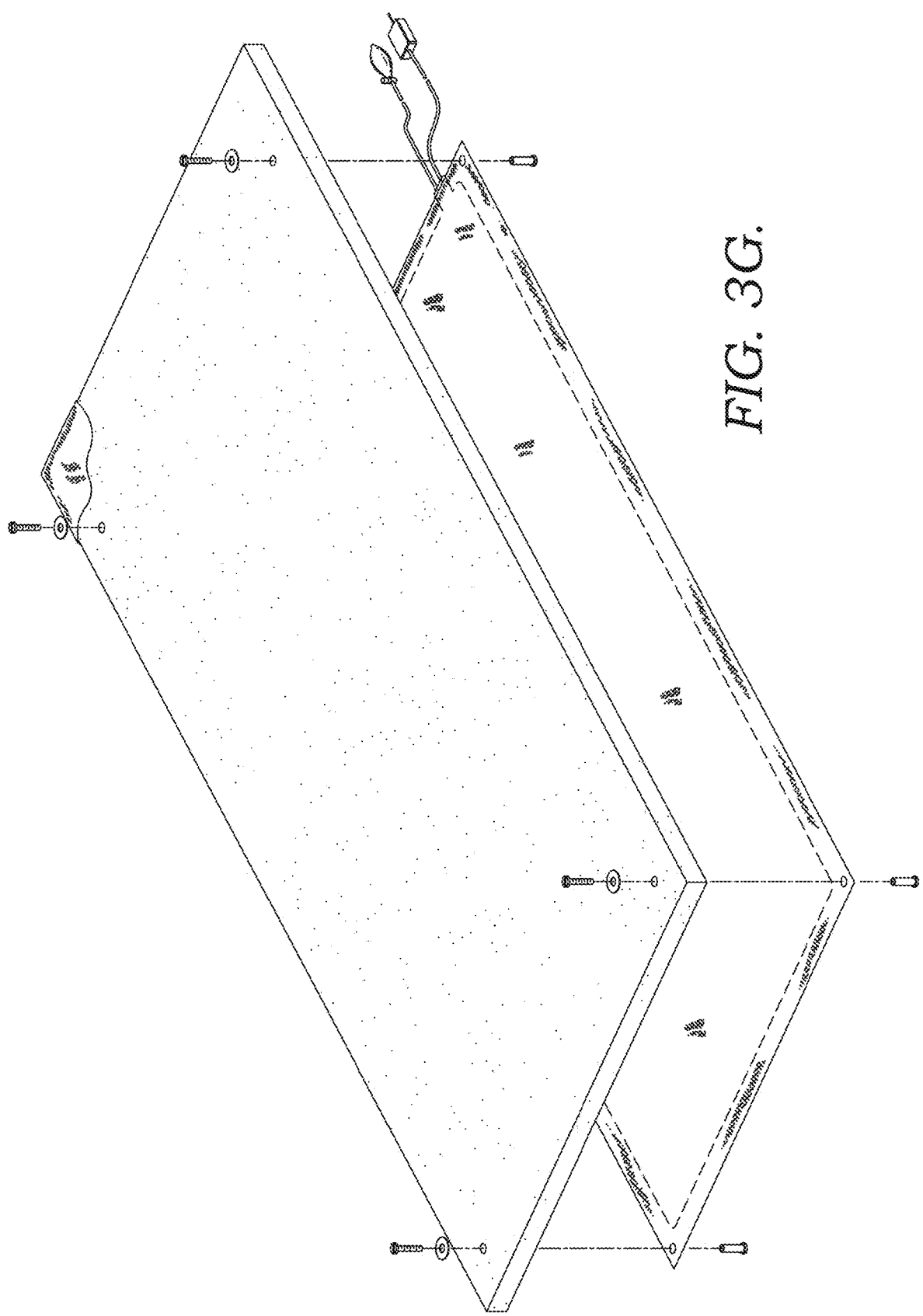

In some embodiments, air bladder 320 may include a pump 335 and a release value 333. Additional aspects of example support surfaces are depicted in FIGS. 3B-3G. In particular, FIG. 3B includes an outer seat-cushion surface 311, a cushion layer 341, cover 351, an air bladder layer 321a and 321b coupled to pressure sensor(s) component 330, and may also include pressure pump 335a, pressure release value 333a. FIG. 3C includes an outer mattress or pad surface 312, a cushion layer 342, cover 352, an air bladder layer 322a and 322b coupled to pressure sensor(s) component 330, and may also include pressure pump 335b, pressure release value 333b. FIGS. 3F and 3G depict additional aspects of example support surfaces.

With continuing reference to FIG. 1A and FIGS. 3A-3G, in some embodiments, measurement device 141 comprises a medical-grade sphygmomanometer-type air-inflatable rubber bladder, such as example bladder 320, which is rectangular and approximately 18 inches (45 cm) long and 6 inches (15 cm) wide, which may be fixedly or removably affixed to the upper surface of a closed-cell neoprene foam rubber substrate (e.g., cushion layer 340) that is cut so as to have areal dimensions corresponding to the seat cushion. In one embodiment, the cushion layer 340 has a thickness approximately equal to 1 inch (2.54 cm) and having density of 9 lb/ft3, 25% compression strain at 7 psi, and elastomeric shore "OO" indentor rating equal to 50 durometer per ASTM D-3575 testing. In an embodiment, bladder 320 comprises an inflatable bladder and is affixed to and positioned on the cushion layer 340 to be vertically directly under where the user's ischial bones will be positioned when seated. In some embodiments, bladder 320 is equipped with a port that is connected to a length of gas-tight hollow elastomeric tubing 325 and an expansile, hand-squeezable rubber air bulb 335 and finger-operated gas valve 333, such that by way of example and without limitation, a seated user is able to inflate and adjust the bladder to contain a small amount of air, which may be sufficient so that the two sides of the rubber bladder are not in contact with each other under normal conditions of sitting (or laying, in the case of a mattress) and movement upon the cushion assembly (bladder does not "bottom out" as the user moves or leans when sitting). In some embodiments, bladder 320 is furthermore connected to non-distensible tubing whose distal end is connected to the pressure sensor(s) component 330 for the purpose of measuring air pressure within the inflated bladder 320 assembly when the user is seated upon (or lying on) the cushion assembly.

In some embodiments, the bladder-sensor-substrate portions of measurement device 341 (e.g., items 320, 330, and 340 of FIG. 3A) may be placed inside a suitable cover 350, such as a fabric cover. In one example embodiment actually reduced to practice, cover 350 comprises a ballistic nylon sleeve of the same sort that was provided by the manufacturer of the wheelchair seat cushion. The upper fabric surface of the bladder-sensor-substrate module cover was equipped with hook-and-loop fastener patches, in opposing locations to match and mate with corresponding hook-and-loop fastener patches affixed to the underside of the wheelchair seat cushion cover. This enables the bladder-sensor-substrate portions to be accurately and repeatably fastened to a wheelchair seat cushion in such a manner as to insure that the user's anatomy is consistently positioned directly over the bladder-sensor-substrate module when seated. Other removable fastening devices for removably securing portions of the measurement device 341 may be used without departing from the scope of the invention described herein. Likewise, permanent methods of fixing some portions of the measurement device 341 together may be utilized without departing from the scope of the invention described herein. In some embodiments, measurement device 141 includes or operates in conjunction with a wheelchair seat cushion.

In operation, the user sits upon measurement device 141, inflates and adjusts the pressure in the bladder 320. Thereafter, pressure sensor(s) component 330 then may commence acquisition of pressure data. In an example embodiment, the pressure data may be sampled at 20 Hz and used to create a pressure measurements time series. In an embodiment, the pressure measurements time series may be telemetered to a receiving computer 120 and may be stored in storage 121 for ongoing analysis and/or later analysis. In one example embodiment reduced to practice, the pressure data was transferred to a laptop computer's solid-state disk storage as an ASCII file, to which were appended ongoing updates. Successive 2,000-second measurement periods (40,000 samples long) were stored, and spectrum analysis was performed upon the pressure time series from each measurement period, as further described in connection to method 200 of FIG. 2.

Continuing with FIG. 1A, in some embodiments, measurement device 141 may include a Bluetooth or wireless communication data-transfer capability and may be wirelessly communicatively coupled with an application on a computing device, such as a smartphone an app or aspect of decision support application 140. Embodiments of measurement device 141 may store user-derived data locally or communicate data over network 175 to be stored remotely. Some embodiments of measurement device 141 include a monitor interface, which may be embodied as I/O such as buttons and sounds emitted from the measurement device 141, its firmware or software application or app operating on a user's mobile device or computer system 120, and in an embodiment may facilitate uploading of measured (or recorded, or otherwise received) information from measurement device 141 to computer system 120. Additionally, some embodiments of measurement device 141 include functionality for processing user-derived information locally or for communicating the information to computer system 120, where it is processed. In some embodiments, the processing may be carried out or facilitated by one or more software agents, as described below. In some embodiments the processing functionality, performed on measurement device 141 and/or computer system 120 includes pre-processing and/or signal conditioning, such as removing noise or erroneous information.

Example operating environment 100 further includes computer system 120, which may take the form of one or more servers, and which is communicatively coupled through network 175 to EHR system 160, and storage 121.

Computer system 120 comprises one or more processors operable to receive instructions and process them accordingly, and may be embodied as a single computing device or multiple computing devices communicatively coupled to each other. In one embodiment, processing actions performed by system 120 are distributed among multiple locations such as one or more local clients and one or more remote servers, and may be distributed across the other components of example operating environment 100. For example, aspects of application 140 or interface 142 may operate on or utilize computer system 120. Similarly, a portion of computing system 120 may be embodied on user interface 142, application 140, and/or EHR system(s) 160. In one embodiment, system 120 comprises one or more computing devices, such as a server, desktop computer, laptop, or tablet, cloud-computing device or distributed computing architecture, a portable computing device such as a laptop, tablet, ultra-mobile P.C., or a mobile phone.

Embodiments of computer system 120 include computer software stack 125, which in some embodiments operates in the cloud, as a distributed system on a virtualization layer within computer system 120, and includes operating system 129. Operating system 129 may be implemented as a platform in the cloud, and which is capable of hosting a number of services such as 122, 124, 126, and 128. Some embodiments of operating system 129 comprise a distributed adaptive agent operating system. Embodiments of services 122, 124, 126, and 128 run as local services or may be distributed across one or more components of operating environment 100, in the cloud, on one or more personal computers or servers such as system 120, and/or a computing device running interface 142 or application 140. In some embodiments, interface 142 and/or application 140 operate in conjunction with software stack 125.

In embodiments, model variables indexing (or mapping) service 122 facilitate retrieving patient variables such as physiological or other measurements, which may include frequent item sets, extracting database records, and/or cleaning the values of variables in records. For example, service 122 may perform functions for synonymic discovery, indexing or mapping variables in records, or mapping disparate health systems' ontologies, such as determining that a particular medication frequency of a first record system is the same as another record system. Predictive models service 124 in general is responsible for providing models such as multi-variable models, for detecting or predicting a pressure-injury event or conditions prone to causing or exacerbating pressure injury. In some embodiments, services 122 and/or 124 may invoke computation services 126.

Computation services 126 may perform statistical software operations, and may include statistical calculation packages such as, in one embodiment, the R system (the R-project for Statistical Computing, which supports R-packages or modules tailored for specific statistical operations, and which is accessible through the Comprehensive R Archive Network (CRAN) at http://cran.r-project.org) or similar services. In an embodiment, computation services 126 and predictive models service 124 include the services or routines, which may be embodied as one or more software agents or routines such as the example embodiments of computer program routines illustratively provided in FIGS. 7A-10. In one embodiment, computation services 126 comprises the R-System psd package for performing power spectral density estimation, and segmented package for determining cut-points (e.g., breakpoints) or segments in a regression model. Both of these example computation services are utilized on a time series of cushion pressure measurements in the example computer program routines of FIGS. 7A-B, 8A-B, and 9A-B.

Computation services 126 also may include natural language processing services (not shown) such as Discern nCode' developed by Cerner Corporation, or similar services. In an embodiment, computation services 126 include the services or routines, which may be embodied as one or more software agents or computer software routines such as the example embodiments of computer program routines illustratively provided in FIGS. 7A-10. Computation services 126 also may include services or routines for utilizing one or more prediction or detection models or methods, such as described in connection to FIG. 2 and the example computer program routines illustratively provided in FIGS. 7A-10. In some embodiments, computation services 126 use EHR system(s) 160, model data and model storage services (not shown), and/or other components of example operating environment 100, and may also include services to facilitate receiving and/or pre-processing physiological (or other patient-related) data. For instance, model data and model storage services may be utilized to perform services for facilitating storage, retrieval, and implementation of the forecasting models described herein and of the data used in the models or predictive services.

In some embodiments, stack 125 includes file system or cloud-services 128. Some embodiments of component 128 may comprise an Apache Hadoop and Hbase framework, or similar frameworks operable for providing a distributed file system, and which in some embodiments facilitate provide access to cloud-based services, such as those provided by Cerner Healthe Intent®. Additionally or alternatively, some embodiments of file system or cloud-services 128 or embodiments of stack 125 may comprise one or more stream processing service(s). For example, such stream processing service(s) may be embodied using IBM InfoSphere stream processing platform, Twitter Storm stream processing, Ptolemy or Kepler stream processing software, or similar complex event processing (CEP) platforms, frameworks, or services, which may include the user of multiple such stream processing services (in parallel, serially, or operating independently). Some embodiments of the invention also may be used in conjunction with Cerner Millennium®, Cerner CareAware® (including CareAware iBus®), Cerner CareCompass®, or similar products and services.

Example operating environment 100 also includes storage 121 (or data store 121), which in some embodiments includes patient data for a candidate or target patient (or information for multiple patients), including raw and processed patient data; variables associated with patient diagnoses or determinations, recommendations; recommendation knowledge base; recommendation rules; recommendations; recommendation update statistics; an operational data store, which stores events, frequent itemsets (such as "X often happens with Y", for example), and item sets index information; association rulebases; agent libraries, solvers and solver libraries, and other similar information including data and computer-usable instructions; patient-derived data; and health care provider information, for example. It is contemplated that the term data includes any information that can be stored in a computer-storage device or system, such as user-derived data, computer usable instructions, software applications, or other information. In some embodiments, data store 121 comprises the data store(s) associated with EHR system 160. Further, although depicted as a single storage data store, data store 121 may comprise one or more data stores, or may be in the cloud.

Figure 1B:
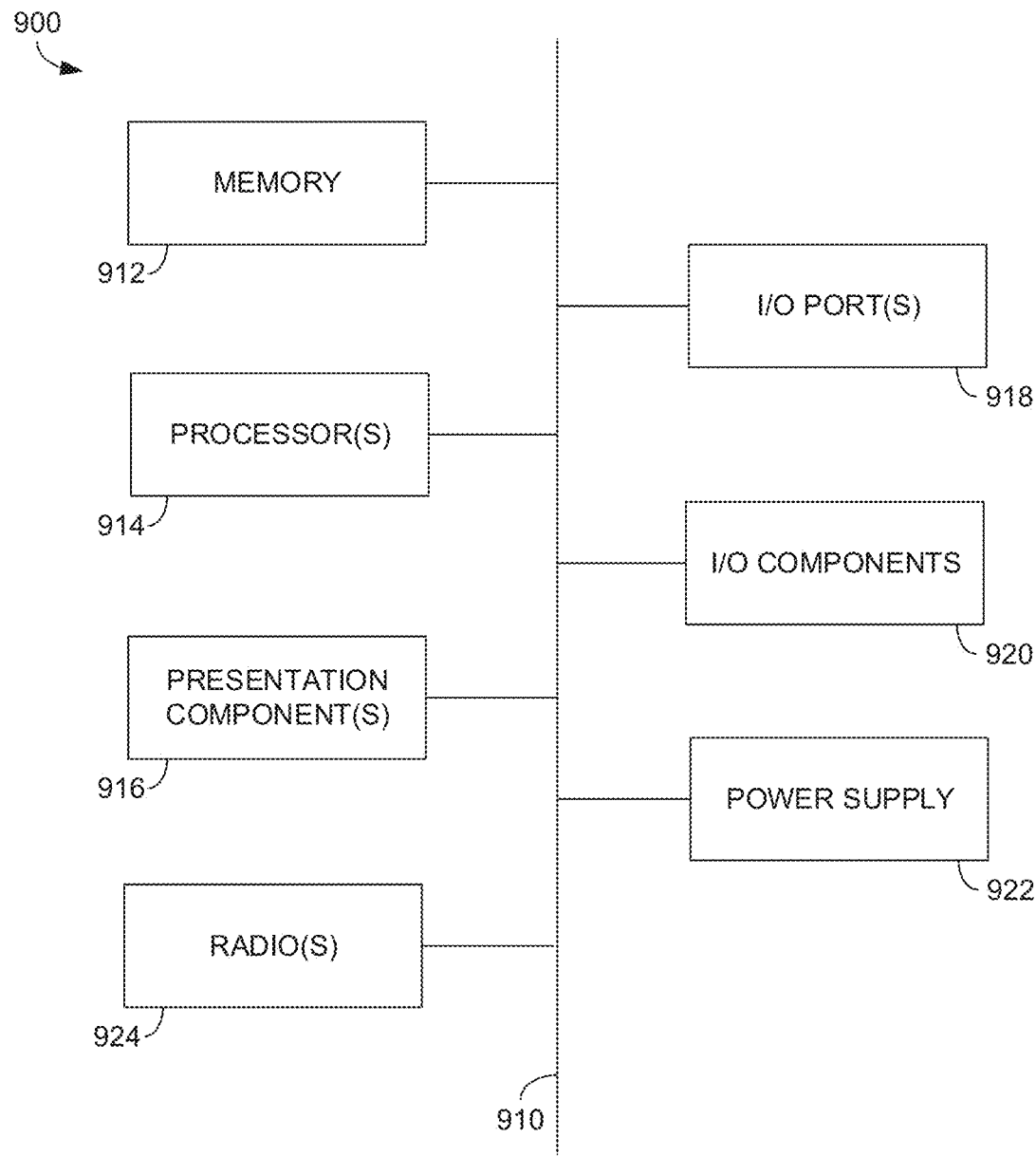

Turning briefly to FIG. 1B, there is shown one example embodiment of computing system 900 representative of a system architecture that is suitable for computer systems such as computer system 120. Computing device 900 includes a bus 910 that directly or indirectly couples the following devices: memory 912, one or more processors 914, one or more presentation components 916, input/output (I/O) ports 918, input/output components 920, radio 924, and an illustrative power supply 922. Bus 910 represents what may be one or more busses (such as an address bus, data bus, or combination thereof). Although the various blocks of FIG. 1B are shown with lines for the sake of clarity, in reality, delineating various components is not so clear, and metaphorically, the lines would more accurately be grey and fuzzy. For example, one may consider a presentation component, such as a display device, to be an I/O component. Also, processors have memory. As such, the diagram of FIG. 1B is merely illustrative of an example computing system architectures that can be used in connection with one or more embodiments of the present disclosure. Distinction is not made between such categories as "workstation," "server," "laptop," "hand-held device," etc., as all are contemplated within the scope of FIG. 1B and reference to "computing system."

Computing system 900 typically includes a variety of computer-readable media. Computer-readable media can be any available media that can be accessed by computing system 900 and includes both volatile and nonvolatile media, and removable and non-removable media. By way of example, and not limitation, computer-readable media may comprise computer storage media and communication media. Computer storage media includes both volatile and nonvolatile, removable and non-removable media implemented in any method or technology for storage of information such as computer-readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by computing system 900. Computer storage media does not comprise signals per se. Communication media typically embodies computer-readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of any of the above may be included within the scope of computer-readable media.

Memory 912 includes computer-storage media in the form of volatile and/or nonvolatile memory. The memory may be removable, non-removable, or a combination thereof. Exemplary hardware devices include solid-state memory, hard drives, optical-disc drives, etc. Computing system 900 includes one or more processors that read data from various entities such as memory 912 or I/O components 920. In an embodiment, storage 121 is embodied as memory 912. Presentation component(s) 916 present data indications to a user or other device. Exemplary presentation components include a display device, speaker, printing component, vibrating component, etc. In an embodiment, functionality provided via user/clinician interface 142 is facilitated by one or more presentation components 916.

In some embodiments, computing system 924 comprises radio(s) 924 that facilitates communication with a wireless-telecommunications network. Illustrative wireless telecommunications technologies include CDMA, GPRS, TDMA, GSM, LTE, WiMAX, and the like. Radio 924 may additionally or alternatively facilitate other types of wireless communications including Wi-Fi, Bluetooth, NFC, other types of RF communication, light, infrared, or the like. As can be appreciated, in various embodiments, radio 924 can be configured to support multiple technologies and/or multiple radios can be utilized to support multiple technologies.

I/O ports 918 allow computing system 900 to be logically coupled to other devices, including I/O components 920, some of which may be built in. Illustrative components include a microphone, joystick, game pad, satellite dish, scanner, printer, wireless device, etc. The I/O components 920 may provide a natural user interface (NUI) that processes air gestures, voice, or other physiological inputs generated by a user. In some instances, inputs may be transmitted to an appropriate network element for further processing. An NUI may implement any combination of speech recognition, stylus recognition, facial recognition, biometric recognition, gesture recognition both on screen and adjacent to the screen, air gestures, head and eye tracking, and touch recognition (as described in more detail below) associated with a display of the computing system 900. The computing system 900 may be equipped with depth cameras, such as stereoscopic camera systems, infrared camera systems, RGB camera systems, touchscreen technology, and combinations of these, for gesture detection and recognition. Additionally, the computing system 900 may be equipped with accelerometers or gyroscopes that enable detection of motion.

The architecture depicted in FIG. 1B is provided as one example of any number of suitable computer architectures, such as computing architectures that support local, distributed, or cloud-based software platforms, and are suitable for supporting computer system 120.

Returning to FIG. 1A, in some embodiments, computer system 120 is a computing system made up of one or more computing devices. In some embodiments, computer system 120 includes one or more software agents, and in an embodiment includes an adaptive multi-agent operating system, but it will be appreciated that computer system 120 may also take the form of an adaptive single agent system or a non-agent system. Computer system 120 may be a distributed computing system, a data processing system, a centralized computing system, a single computer such as a desktop or laptop computer or a networked computing system.

Figure 2:
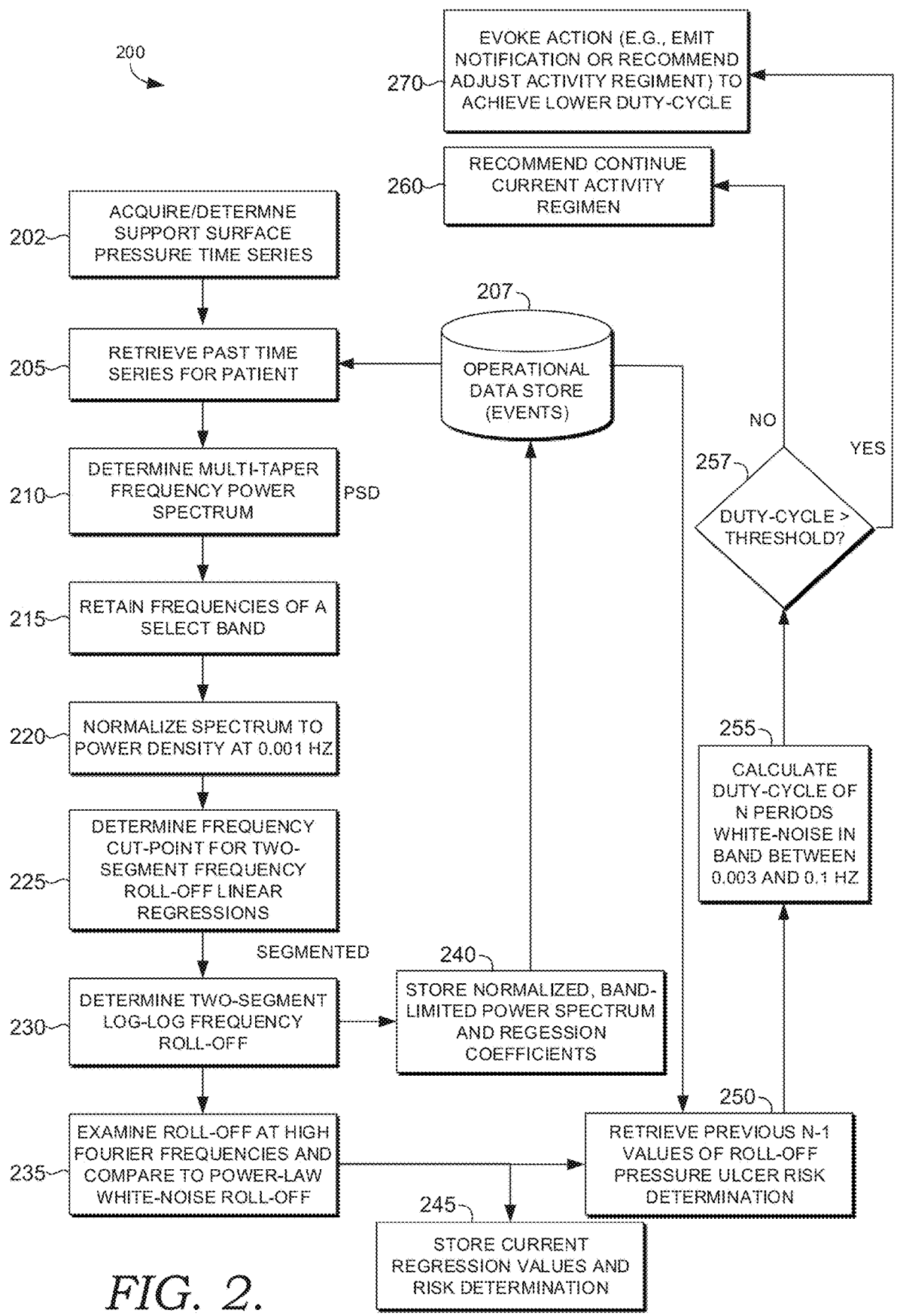
FIG. 2 depicts a flow diagram of a method for conditionally generating a notification regarding a patient's risk for pressure injury based, in accordance with an embodiment of the disclosure.

Turning now to FIG. 2, one example embodiment of a method 200 for conditionally generating a notification regarding a patient's risk for pressure injury. In particular, method 200 may be employed to automatically ascertain whether the patterns of movements of a human patient, whose weight is supported on a support surface, exhibit sufficient frequency and variability of activity such as will confer either certain health benefits or expose the individual to certain health risks, such as development of pressure ulcers in the load-bearing skin and soft tissues. Accordingly, embodiments of method 200 utilize an embodiment of a pressure measurement device such as measurement device 141 described in connection to FIG. 1A and the aspects of measurement devices 141 depicted in FIGS. 3A-3G.

Example method 200 begins at step 202, wherein support surface pressure time series data are acquired. Embodiments of step 202 utilize a pressure measurement device, such as measurement device 141 described previously, to obtain a series of pressure measurements for a human target, such as a patient sitting on an embodiment of measurement device 141 embodied as a wheelchair cushion. Thus, measurements of pressure associated with mechanical loading of a support surface by suprajacent body parts of a person may be used to determine patterns of load-bearing and moment-to-moment adjustments of position. The measurements may be received continuously, periodically, at intervals, or as needed. In an embodiment, measurements are obtained at a frequency of 20 Hz. In an embodiment, the sampling measurement rate is at least 10 times the Nyquist frequency of the highest-frequency of the spectral band of interest with regard to pressure ulcer development, such as further described herein. Some embodiments of step 202 may further include associating a particular patient with the measurement device 141, and/or binding information about the patient or patient's EHR and initializing a data.frame (e.g., attirbutes and current date) for acquiring the pressure data.

At step 205, retrieve time series of pressure data for the patient and over a set of previous time intervals or time periods. In some embodiments, the set of time-periods may comprise consecutive or substantially consecutive time intervals. For instance, in one embodiment, the consecutive time-periods are approximately between 15 and 30 minutes. Other time intervals are also contemplated; such time intervals may be sufficiently long so that, if movements are inadequate to relieve focal pressure within tissues supporting the load exceeding the closing pressure for small blood vessels within the tissues, ischemia and/or ischemia-reperfusion injury are likely to develop. Chronic, frequently repeated or unremitting episodes of such ischemic exposures are causally related to injury and non-healing of the load-bearing tissue structure. Embodiments of step 205 may retrieve the past time series data from an operational data store 207, which may be embodied as storage 121 or the patient's EHR 160.

At step 210, determine multi-taper frequency power spectrum on the time series information. In an embodiment, for a first time-period in the set of time periods, such as the current time-period or the most recent time-period, or upon acquiring time series information for a new time period, a multi-taper filtered power spectral density is determined over a select frequency band. As described herein, operational aspects of embodiments of this disclosure depend on a capability of distinguishing power-law properties of the frequency power spectrum at different frequency bands. Therefore the measurement system, such as measurement device 141, that is utilized in method 200 (and in particular with step 202), is able to acquire measurements that will enable the system to distinguish white-noise-like spectra associated with pressure-ulcer-proneness (e.g., in the upper band from approximately 0.003 Hz to 0.1 Hz) from black- or brown-noise-like spectra in the same band, which characterizes a pattern of movements that are actually protective against the formation or pressure injury.

But quantization noise associated with analog-to-digital conversion (ADC) in data has its own frequency power spectrum. This quantization noise spectrum is determined by the ADC sampling frequency and the size of the smallest quantum or step between adjacent levels in the ADC's least-significant bit (LSB). Therefore, in order to avoid an error, the measurement circuitry of measurement device 141 (e.g., in an embodiment this circuitry may comprise or utilize the transducer 339 and pressure sensor 337a shown in FIGS. 3E and 3D, respectively) may have an LSB size that is smaller than the meaningful variations in the signal that is to be measured. Likewise, measurement device 141 (or its measurement circuitry) should be operated at a sampling frequency that is higher than the minimum Nyquist rate (where $f_N$, is the Nyquist frequency of data acquisition time series of sampled measurements).

In some embodiments for addressing pressure-ulcer-related risk in a sitting position for tissues in contact with a support surface such as a wheelchair seat, an ADC with an LSB quantum size of 0.04 kPa (0.3 mmHg) or smaller is utilized on a sensor device having a full-scale dynamic range from 0 to 60 psia (approximately 3100 mmHg, 4.1 atm, or 413 kPa), which in turn entails a resolution or precision of at least 13 bits in the sensor and analog-to-digital converter circuitry across this range of pressures. For example, an embodiment actually reduced to practice utilizes a measurement device 141 with a DLV-060A pressure sensor by All Sensors Inc.® having a 14-bit ADC operating in the range 0-60 psia.

The power spectrum of a quantizer output is equal to the power spectrum of the input signal, plus the power spectrum of the quantization noise. The quantization noise power spectrum is flat with respect to frequency and has a total power equal to $q^2/12$ where q is the LSB quantum size in the units of measurement. In general, quantization noise power spectra of contemporary ADC circuitry exhibit approximately white-noise flat ($1/f^0$) power-law behavior. In connection with the linear superposition of quantization-noise and input signal, it is desirable that the total power of the quantization noise be substantially smaller than the power of the input signal in the bands of interest, between about 0.001 Hz and 0.10 Hz. In an embodiment, the total power of the ADC quantization noise is less than 10% of the power of the input signal between about 0.001 Hz and 0.10 Hz.

Accordingly, at step 215 frequencies of a select band are retained. For example, in an embodiment, the retained frequency band is between 0.001 Hz and 0.03 Hz, and spectrum frequency values below 0.001 Hz and above 0.10 Hz are discarded. At step 220, the power spectrum for these frequencies then may be normalized. In embodiments where normalization is performed, the determined power spectrum at the remaining frequencies of the selected band may be normalized to the power spectral density at 0.001 Hz, such as by setting the value at 0.001 Hz to be equal to 1.0. In some embodiments, the resulting pressure power spectrum for the first time-period may transformed as a log-log matrix. For instance, in an embodiment it may be transformed with spectral density in dB for each value of log 10(frequency).

At step 225, determine frequency cut-point for two-segment frequency roll-off linear regressions. In embodiments of step 225, for the current pressure power spectrum, a linear regression of two piecewise line-segments maybe calculated, in the retained frequency band (e.g., between 0.001 Hz and 0.1 Hz). In an embodiment of step 225, a least-squares or similar method is utilized. An optimal cut-point is determined separating the slide-segments. In some embodiments of step 225, the segmented package (computational services 126) may be utilized to facilitate determining the cut-point, as described above and shown in connection to FIGS. 7A-B, 8A-B, and 9A-B. Illustrative examples showing the output of step 225 and in particular, optimal cut-points and regression segments are depicted in in graphs 501, 520, and 530 of FIGS. 5A-5C (corresponding to normal movement, showing cut-points 505 and segments 503 and 507 for FIG. 5A; showing cut-points 525 and segments 523 and 527 for FIG. 5B; and showing cut-points 535 and segments 533 and 537 for FIG. 5C) and graphs 540, 550, and 560 of FIGS. 5D-5F (corresponding to movement likely to cause or worsen pressure injury, showing cut-points 545 and segments 543 and 547 for FIG. 5D; showing cut-points 555 and segments 553 and 557 for FIG. 5E; and showing cut-points 565 and segments 563 and 567 for FIG. 5F). The line-segment regression coefficients for the current power spectra may be stored in step 240, with the regression determinations from previous power spectra, for use in subsequent steps of method 200.

At step 230, determine the two-segment log-log frequency roll-off. In embodiments of step 230, a first-order (slope) coefficient for the segments' linear regressions may be determined and in step 235 may be compared to characteristic white-, pink-, brown-, and black-noise α values for $1/f^\alpha$ power roll-off. For example, in an embodiment, $\alpha \in (-0.6,+0.4]$, $\alpha \in (+0.4,+1.4]$, $\alpha \in (+1.4,+2.0]$, and $\alpha > +2.0$, respectively), such as shown in FIG. 4. Based on this comparison in step 235, it may be inferred that the instant time-period has conditions for forming pressure-ulcers. In particular, in one embodiment, if the slope coefficient in the frequency band between 0.003 Hz and 0.10 Hz matches a $1/f^\alpha$ power roll-off of $\alpha \in (-0.6,+0.4]$, then it is determined that the condition for the time period associated with this power spectrum is pressure ulcer-prone. That is, the patient is at risk for developing pressure injury. Accordingly, such embodiments function as a sensor (e.g., a smart sensor) by more accurately detecting, using the algorithm described above and including the comparison, those dangerous conditions which may promote ulcer formation (or impede healing). Similarly, these embodiments more accurately detect healthy conditions unlikely to promote ulcer formation.

At step 245, the current regression values and risk determination (or likelihood of forming pressure injury) determined in step 235 are stored. At step 250 the regression coefficients from N−1 time periods' pressure spectra (or previous pressure-injury-risk determinations) for previous (or prior) N−1 time periods are received. The received data may be retrieved from operational data store 207, which may be embodied as storage 221 or the patient's EHR 160.

At step 255, a duty-cycle may be determined of patterns whose frequency spectra are associated with pressure ulcer proneness. In particular, a duty-cycle of high-frequency pressure-ulcer-prone white-noise spectrum condition among the first (or current) time-period's regression values and the N−1 previous time-period's regression values. For example, the duty cycle may be determined as a daily cumulative percentage of time. In an embodiment, a duty-cycle of N periods (N−1 precious time periods and the current or a recent time period, N) is determined of high-frequency white noise spectrum (indicating pressure-ulcer-prone conditions) in a frequency band between 0.003 and 0.1 Hz.

At step 257, where the duty cycle of the high-frequency pressure-ulcer-prone white-noise spectrum condition exceeds a threshold value, then it may be inferred that tissue breakdown occurs and pressure ulcers are likely to form. Similarly, if pressure ulcers are already present in the affected skin and soft tissue, the pressure ulcers are unlikely to heal. The threshold may be pre-determined, determined by a clinician, or determined based on a condition of the patient. For instance, a patient that is determined to be more prone to pressure injury (or a patient already having pressure injury) may have a lower threshold. Similarly a heavier patient may have a lower threshold than a lighter patient. In an embodiment, a threshold of duty-cycle of fifty percent is utilized.

If the threshold is not satisfied, then method 200 proceeds to step 260 and the patient may continue his or her present course because there is no (or little) risk of pressure injury forming. But if the threshold is satisfied or exceeded, then method 200 proceeds to step 270. At step 270, At step 270, an action may be evoked, for example a notification may be emitted or a recommendation generated and provided, such as for the patient to alter their activity so as to create helpful movement that reduces the risk of pressure injury. In one embodiment of step 270, a notification may be provided or another intervening action may be initiated. For instance, one intervening action comprises generating a notification that may be emitted or otherwise communicated to the patient or to a caregiver, such as a provider clinician responsible for the care of the patient. For example, an electronic advisory or warning message may be emitted to a human user, such as a caregiver, indicating an elevated risk of pressure injury to the user, to encourage the user to initiate more frequent movements of position with respect to the load-bearing support surface. In an embodiment, the action comprises generating and emitting or communicating the notification, which may be emitted/communicated via a bedside or patient-side alarm, user/clinician interface (such as interface 142 described in FIG. 1A), or may be communicated to a smartphone or personal computing device of a caregiver, thereby alerting them of an impending deterioration of the patient's condition. In one embodiment, the notification comprises an event signal and includes the likelihood of future pressure injury to the user. In some embodiments, the intervening action comprises adaptively providing notification at irregular within-day intervals. In particular, the irregular intervals may be more likely—verses regularly or predictably provided alerts—to provoke a positive response to establish, restore, or sustain healthy patterns of movement and pressure-relief from the load-bearing tissues in contact with the support surface.

Another action that may be initiated, based on the determined likelihood, comprises a recommendation for modifying a care plan or treatment procedure associated with the patient; for example, a recommendation may comprise one or more movements or activity to be performed by the patient or by a caregiver to the patient, increasing patient monitoring or level of care, operating on the patient, or administering another similarly effective therapeutic intervention. The recommendation may be provided in conjunction with a notification, and/or may be provided via a user/clinician interface, such as interface 142, described in connection with FIG. 1A.

Yet another action that may be initiated, based on the determined likelihood, comprises automatically modifying computer code executed in a healthcare software program for treating the patient, thereby transforming the program at runtime. For example in one embodiment, the modification comprises modifying (or generating new) computer instructions to be executed at runtime in the program, the modification may correspond to a change in a care plan, treatment procedure, or therapeutic intervention to be administered to the patient due to the determined likelihood of pressure injury occurrence. In one instance, the modification comprises changing the executed computer instructions corresponding to monitoring the patient's condition, such as increasing the frequency of obtaining physiological measurements of the patient, or increasing sensitivity of monitoring physiological changes in a patient.

Yet another action that may be initiated, based on the determined likelihood, comprises scheduling healthcare resources for the patient. For example in one embodiment, a physical therapy resource may be automatically reserved for the patient, healthcare staff may be notified and/or automatically scheduled, or transportation/support staff or resources for getting the patient to a healthcare facility may be called. In one embodiment, this action comprises modifying or updating a resource/scheduling electronic record in a resource/scheduling system, such as operated as part of a hospital or healthcare system. In one embodiment, the action comprises, upon a determined likelihood of a future pressure injury or event occurrence, initiating a computer instruction that modifies the scheduling healthcare resources, which may include computer instructions for automatically alerting, scheduling, and/or notifying staff, reserving rooms, transportation, or other equipment/space, and which may include changing the priority of the patient (when compared to other patients) for receiving these resources.

Example Reduction to Practice

With reference to FIGS. 3A, 4, 6A-6C, 7A-10, and 12, and with continuing reference to method 200 of FIG. 2 an example is provided of an embodiment of the disclosure constructively reduced to practice. Here, computer system 120 running the Linux operating system (129) was utilized with the open-source statistical software package R, and the R modules psd and segmented (computation services 126). This example embodiment used the example computer program routine provided in FIGS. 7A-7B; 8A-B; and 9A-B.

This example implementation was for a human user seated in a wheelchair in a sitting position on a seat cushion support surface (e.g., a support surface comprising measurement device 141); however, as described herein, other embodiments could equally well be applied to a human user lying upon a bed in a recumbent position on a mattress support surface or other arrangement, such as shown in the example mattress 302 of FIG. 3C. The measurement device 141 in this example reduction-to-practice includes an All Sensors Inc DLV-060A with a 14-bit ADC operating in the range 0-60 psia.

Further, in this example embodiment, to insure that the "floor" of the power density at 0.1 Hz that is related to ADC quantization noise is preferably at least 3 dB below the power of typical seated support surface pressure signal fluctuations at 0.1 Hz (Nyquist frequency $f_N=2*0.1$ Hz=0.2 Hz), a sampling rate $f_S>10*f_N$ is needed. This example reduction to practice implementation utilizes $f_S=100*f_N=20$ Hz. Under such conditions, the autocorrelation of the quantizer output is equal to the autocorrelation of the input signal plus the autocorrelation of the quantization noise, such that the transition of the resulting spectrum to a white-spectrum associated with ADC quantization occurs in a high-frequency band that is more than a decade in log 10-frequency above the 0.003 Hz to 0.10 Hz region of interest.

In operation, successive 2,000-second measurement periods (40,000 samples long) were stored, and spectrum analysis was performed upon the pressure time series from each measurement period, such as described in connection to method 200 of FIG. 2. This was performed on 6 wheelchair-bound "experimental" volunteer subjects (4 men and 2 women; aged 29 to 45 years; weight between 161 and 252 lb.) whose care was provided in Cerner Corporation's employee health clinic. These volunteers were studied for a period of 180 days during 2017, during which time 2 volunteers experienced newly-incident pressure ulcers on buttocks and/or sacral regions of skin and soft tissue in contact with the wheelchair support surface. Also studied during this same time period were 6 healthy ambulatory "control" volunteer subjects (3 men and 3 women), also attending Cerner's clinic (aged 30 to 53 years; 145 to 202 lb.), whose roles involved sedentary, seated work for the majority of each working day. Members of "experimental" and "control" groups granted informed consent for the study, and the study was conducted in conformity with applicable Good Clinical Practices (GCP) regulations under the supervision of the Medical Director of Cerner's occupational health clinic. The wheelchair cushions provisioned to both "experimental" and "control" groups were closed-cell Jay "Basic Wheelchair Cushions"® (model SM-300, 18 in. wide left-to-right×16 in. deep front-to-back, enclosed in a black ballistic nylon fabric cover).

Data analysis for this example implementation actually reduced to practice with these "experimental" and "control" groups was accomplished using the computer program routines depicted in FIGS. 7A-B, 8A-B, and 9A-B, which use the R open-source statistical software package psd to calculate multi-taper filtered power spectral density within a frequency band between 0.001 Hz and 0.03 Hz. The R package segmented is used to calculate two-segment linear regressions of the log-transformed power spectra and to determine the optimal cut-point separating the two line-segments. The first-order (slope) coefficient for the segments' linear regressions are then compared to characteristic white-, pink-, brown-, and black-noise α α values for $1/f^\alpha$ power roll-off with frequency $\alpha \in (-0.6,+0.4]$, $\alpha \in (+0.4,+1.4]$, $\alpha \in (+1.4,+2.0]$, and $\alpha>+2.0$, respectively). While simple comparison of each regression segment slope to these a ranges was used for the reduction to practice, such as illustratively depicted in FIGS. 6A-6C (from which it can clearly be seen that there are differences in slope from the pressure ulcer (PU) vs. normal time series power spectra), other embodiment may utilize analysis of variance (ANOVA or ANCOVA) to statistically determine agreement of the measured slope with characteristic a values.

Figure 12:
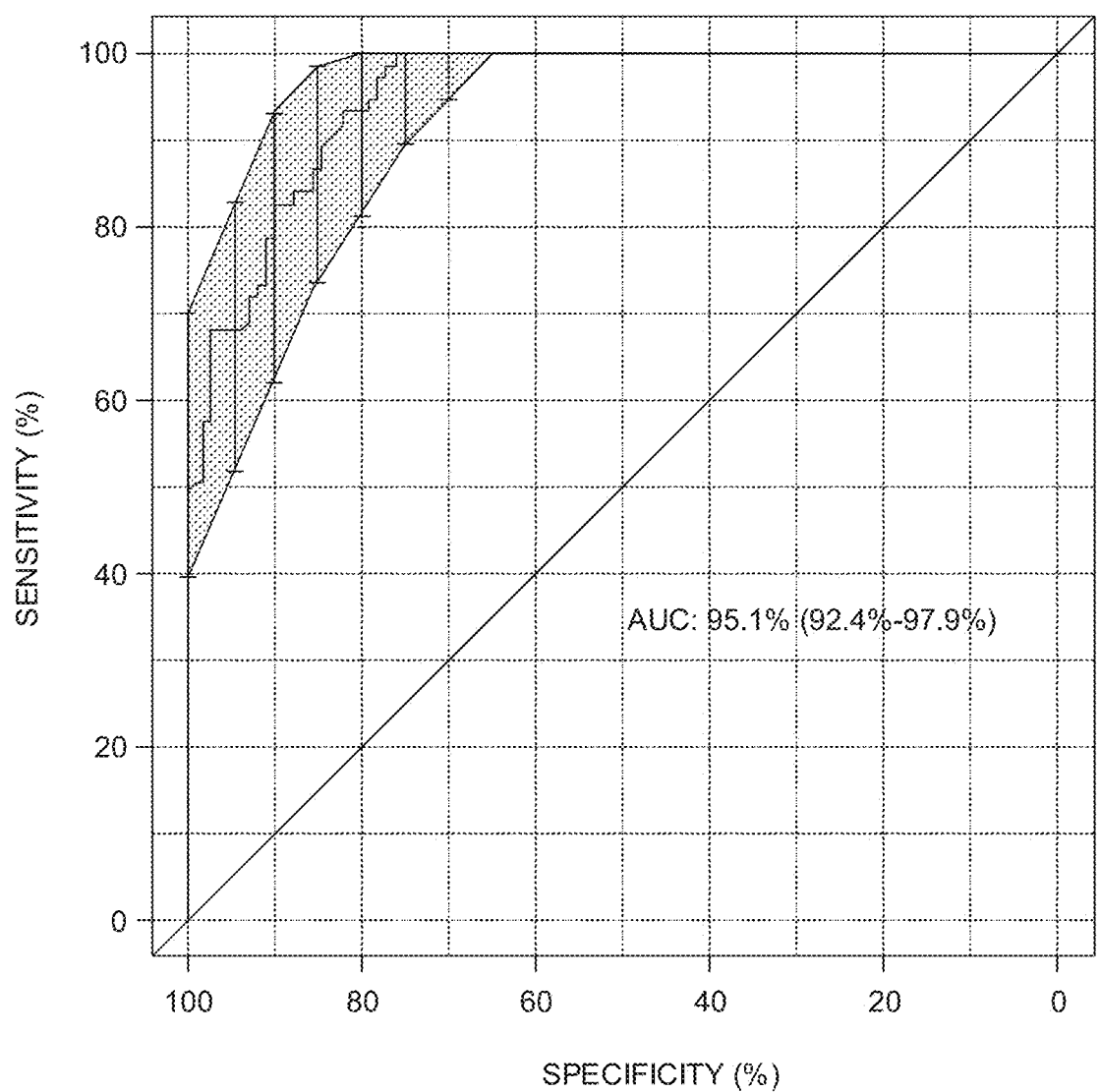
FIG. 12 depicts statistical performance of an example embodiment of the present disclosure actually reduced to practice, including a receiver operating characteristic (ROC) curve, generated using the example computer program routine of FIG. 10, and indicating an improvement over conventional technologies.

A duty-cycle exceeding 50% for any 10 successive 2,000-second segments of pressure measurement was a basis in the reduction-to-practice for emitting advisory messages about increased pressure ulcer risk and a need to move about more frequently in the seated position, or to ambulate if the subject was able to rise from the chair and walk at least briefly. The threshold of duty-cycle=50% was also utilized for the purpose of calculating the receiver operating characteristic (ROC) curve, as shown in FIG. 12, for the purpose of ascertaining the statistical accuracy of the risk-predicting system and method.

Other embodiments of the invention as described herein may include any of the following features. Specifically, the invention herein may be a system for determining a likelihood of a condition for inducing pressure ulcers comprising a measurement device having one or more sensors configured to measure pressure from the weight of a human patient; a processor; computer memory having instructions stored thereon that when executed by the processor perform operations comprising: acquire a series of pressure measurements from the measurement device to determine a set of pressure measurement time series including a first time series comprising pressure measurements for a first time interval and one or more previous time series corresponding to pressure measurements received during one or more previous time intervals; determine a multi-taper frequency power spectrum utilizing the first time series; determine a linear regression for two piece-wise linear segments of the power spectrum, and based on the regressions, the two segments joining at a frequency cut-point, and each regression having a first-order coefficient; utilize the regression coefficients to perform a comparison against noise alpha values; based on the comparison, determine that the first time period has conditions likely to induce pressure injury; and evoke an action based on the determined likelihood that the first time period has conditions likely to induce pressure injury. The noise alpha values can comprise white-, pink-, brown-, and black-noise $\alpha$ values for $1/f^{\alpha}$ power roll-off. The multi-taper frequency power spectrum can be determined over a frequency band of 0.003 to 0.1 Hz. The pressure measurements acquired from the measurement device can be sampled at a rate of at least 20 Hz.

Additionally or alternatively, some embodiments of the invention include a smart sensor for detecting conditions likely to result in pressure injury to a human patient, comprising: a pressure sensor; a pressure transducer coupled to the pressure sensor; an air bladder configurable to hold a volume of air that is in contact with the pressure transducer; a support surface comprising a cushion substrate attached to and below the air bladder; a processor; computer memory having instructions stored thereon that when executed by the processor perform operations comprising a step of determining a series of pressure measurements of the air bladder utilizing the pressure sensor.

Additionally or alternatively, some embodiments of the invention include a system for detecting conditions likely to result in pressure injury to a human patient, comprising: a multi-layer support surface supporting comprising at least one gas-tight inflatable elastomeric bladder positioned subjacent to weight-bearing parts of the human anatomy; a control system including one or a plurality of sensors that generate pressure data signals indicative of continuous pressure within the at least one inflatable bladder arising from a person's body tissue supported by the support surface; a processor operatively coupled to the pressure sensor or sensors and the associated analog-to-digital conversion apparatus, the processor being configured to execute operating logic to determine the pressure frequency spectrum from time series measurements by the sensor apparatus, to band-limit the frequency range of the spectrum so determined, to normalize said band-limited spectrum, to determine a frequency roll-off of the power spectrum by two-segment linear regression on a log-log scale as a function of the data signals, to store said band-limited normalized power spectra and regression coefficients, to compare the regression coefficients for each such power spectrum to power-law roll-off exponents corresponding to white, pink, brown, and black-noise spectral exponents, to retrieve a series of such comparisons, to determine the duty-cycle of segments of said series that correspond to a spectral pattern in the upper frequency band that is associated with excess risk of development of, or non-healing of, pressure injury, and to emit an electronic advisor or warning message in the event that the duty-cycle exceeds a threshold associated with development of, or non-healing of, pressure injury.

The system can further comprise an inflating mechanism to inflate and adjust gas pressure within the inflatable bladder. The control system and processor system can be coupled to an electronic medical record (EMR) over a network and receives information from the EMR for use by the processor in associating the multi-layer support surface and associated apparatus with a particular person and associating the apparatus and information determined from the pressure time series and power spectra with said person, for the purpose of recording the emitted advisory messages and determinations of pressure ulcer risk. The pressure sensor can be attached to the support surface and can measure pressure time series by repeated, periodic, and ongoing sampling in a multi-layer cushion underlying the load-bearing tissues of an individual, in a series of time periods. Each period can be of equal duration T, between 15 and 30 minutes in length. Sampling measurements can be acquired at a sampling rate at least 10 times the Nyquist frequency of the highest-frequency of the spectral band of interest with regard to pressure ulcer development.

Furthermore, transferring the measured pressures in each time period to a computer can be accomplished via a telemetry apparatus utilizing a digital computer interface that is wired, such as a network or USB cable, or can alternatively involve a radiofrequency wireless interface, such as Bluetooth or WiFi or cellular connection to the computer. In some embodiments, after each period ti has elapsed and data transfer has been completed, the computer calculates a multi-taper filtered power spectrum of the pressure time series, by a Fast Fourier Transform or wavelet transform or other means as are known in the art. The spectrum frequency values below 0.001 Hz and above 0.10 Hz can be discarded or ignored in subsequent processing. Furthermore, the calculated power spectrum at the remaining frequencies can be normalized to the power spectral density at 0.001 Hz, setting the value at 0.001 Hz to be exactly equal to 1.0.

The resulting current-period pressure power spectrum as a log-log matrix (with spectral density in dB for each value of log 10(frequency)) can be stored in machine-readable storage associated with the person upon whom the measurements have been made, along with previous power spectra in the system's persistent memory. Furthermore, for the current pressure power spectrum, linear regressions can be calculated for two piecewise line-segments in the frequency band between 0.001 Hz and 0.1 Hz by least-squares or similar methods, as are known to those in the art, to determine the log-log roll-off of power density in dB as a function of frequency in $\log_{10}(Hz)$. The current two line-segment regression coefficient values can be stored in machine-readable storage along with regression determinations from previous power spectra in the system's persistent memory. The first-order (slope) coefficient for the linear regressions can be compared against characteristic white-, pink-, brown-, and black-noise α values for 1/fa power roll-off with frequency a between (0.6,+0.41, a between (0.4,+1.41, a between (1.4,+2.01, and α>+2.0, respectively).

In some embodiments, if the slope coefficient in the frequency band between 0.003 Hz and 0.10 Hz matches a $1/f^\alpha$ power roll-off of a between (0.6,+0.41, then they system can conclude that the condition for the time period associated with this power spectrum is pressure ulcer-prone. The system can retrieve the stored regression coefficients from N−1 time periods' pressure spectra for said person. In some embodiments, the duty-cycle of high-frequency pressure-ulcer-prone white-noise spectrum condition among the current time period's regression values and the N−1 previous time periods' regression values is determined as a numerical percentage of the time periods. Additionally or alternatively, if the duty-cycle of high-frequency pressure-ulcer-prone white-noise spectrum condition exceeds a threshold value, then the system can electronically emit an advisory or warning message to the human user, indicating an elevated risk of pressure injury to the user so as to encourage the user to initiate more frequent movements of position with respect to the load-bearing support surface, such as would result in more effective relief of pressure in the affected skin and soft tissues and prevention of ischemia and/or ischemia-reperfusion injury.

In some embodiments, the multi-layer support surface comprises a contact layer (such as a conventional wheelchair seat and its associated fabric covering), a pressure-measuring layer (comprised of at least one pressure sensor subjacent to load-bearing body parts), and a substrate layer of suitable density and stiffness such as will mechanically isolate the measuring layer from ambient vibrations that may be transmitted through the floor, furniture, or other intervening articles upon which the apparatus is mounted. Furthermore, the control system can receive information regarding ambient conditions proximate to the support surface and modify the pressure measurements as a function of the information regarding the ambient conditions of temperature and atmospheric pressure so as to compensate for artifacts that may arise due to changes in ambient temperature and/or pressure. The inflatable bladder subsystem can be configured to enable adjustment of the internal gas pressure via an elastomeric expansile bulb or other mechanism connected to the at least one inflatable bladder, such that the bladder contains a small amount of pressure above ambient atmospheric pressure so that the bladder does not entirely collapse under support surface load-bearing of the weight of the human user.

The at least one bladder can be affixed to the substrate layer that extends over substantially the entire length and width of the person support surface. Additionally or alternatively, the bladder and substrate layer can be enclosed in a fabric cover of areal dimension substantially the same as the areal dimension of the suprajacent cushion layer and its associated fabric covering. The layers and their fabric coverings can be mechanically joined to each other, so that the apparatus can be periodically disassembled for cleaning or other purposes and accurately reassembled such that serial time periods' measurements of pressures can be made in a controlled and consistent, repeatable manner.

In some embodiments, the calculation of the power spectral density roll-off calculations are performed at ultradian intervals, preferably less than 60 min and more preferably between 15 and 30 min. Each successive determination of power spectral density roll-off measure within a specified time interval can be checked against normative values for persons who develop pressure ulcers and those who do not develop pressure ulcers. Additionally or alternatively, if the duty-cycle of ultradian within-day consecutive determinations showing features associated with pressure ulcer development exceeds a threshold value (in one embodiment, duty cycle>50% denotes increased risk of pressure ulcer formation or non-healing), then that can be used as a trigger to cause the generation of an electronic reminder to prompt the user to commence a increase activity or light exercise in their wheelchair or bed, or ambulate briefly if able to do so. Furthermore, the user's physical activity (or lack thereof) subsequent to receiving an alert or reminder can be ascertained and logged in the device's machine-readable storage for subsequent analysis and personalization of future reminders. In some embodiments, the advisory or warning signal can be emitted to the human user for not less than 10 seconds. The monitoring and analysis of activity variability and of compliance with the emitted reminders can be implemented by periodically synchronizing the monitoring device with data storage and software applications that are present on the user's laptop computer, on a cloud- or web-based host service, or other computational resources.

Many different arrangements of the various components depicted, as well as components not shown, are possible without departing from the spirit and scope of the present invention. Embodiments of the present invention have been described with the intent to be illustrative rather than restrictive. Alternative embodiments will become apparent to those skilled in the art that do not depart from its scope. A skilled artisan may develop alternative means of implementing the aforementioned improvements without departing from the scope of the present invention.

It will be understood that certain features and subcombinations are of utility and may be employed without reference to other features and subcombinations and are contemplated within the scope of the claims. Not all steps listed in the various figures need be carried out in the specific order described. Accordingly, the scope of the invention is intended to be limited only by the following claims.

What is claimed is:

1. A system for determining a likelihood of a condition for inducing pressure ulcers comprising:
   a measurement device having one or more sensors configured to measure pressure from the weight of a human patient;
   a processor; and
   computer memory having computer-usable instructions stored thereon that when executed by the processor perform operations comprising:
      acquire a series of pressure measurements from the measurement device, including pressure measurements received during a first time interval,
      determine a set of pressure measurement time series including a first time series comprising the pressure measurements received during the first time interval;
      determine a multi-taper frequency power spectrum utilizing the first time series,
      determine a linear regression for each of two piecewise linear segments of the power spectrum, each of the regressions having a first-order coefficient, based on the regressions, determine a frequency cutpoint where the two piece-wise linear segments join, perform a comparison against noise alpha values utilizing the regression coefficients, based on the comparison, determine a likelihood that the first time period has conditions likely to induce pressure injury, and initiate an action based on the determined likelihood that the first time period has conditions likely to induce pressure injury.

2. The system of claim 1 wherein the action comprises generating and emitting a notification of an impending deterioration of the patient's condition via a bedside or patient-side alarm, user/clinician interface, or a smartphone or personal computing device of a caregiver.

3. The system of claim 1 wherein the noise alpha values comprise white-, pink-, brown-, and black-noise α values for $1/f^\alpha$ power roll-off.

4. The system of claim 1 wherein the multi-taper frequency power spectrum is determined over a frequency band of 0.003 to 0.1 Hz.

5. The system of claim 1, wherein the pressure measurements acquired from the measurement device are sampled at a rate of at least 20 Hz.

6. The system of claim 1, wherein the first time interval is between 15 and 30 minutes in duration.

7. The system of claim 1, wherein the measuring device comprises:
a multi-layer support surface having:
a contact layer configured for a person to sit or lay thereon comprising a cushion substrate,
a pressure-measuring layer subjacent to the contact layer, and
a substrate layer having a density and stiffness configured to mechanically isolate the pressure-measuring layer from ambient vibrations transmitted through the floor, furniture, or other intervening articles upon which the multi-layer support surface is mounted.

8. The system of claim 7, wherein the pressure-measuring layer comprises:
a pressure sensor;
a communication component that receives pressure measurements from the pressure sensor and sends data corresponding to the pressure measurements to the processor or the computer memory, and
an air bladder inflatable to hold a volume of air that is in contact with the pressure sensor.

9. A system for determining a likelihood of a condition for inducing pressure ulcers comprising:
a measurement device including a multi-layer support surface having:
a contact layer configured for a person to sit or lay thereon comprising a cushion substrate,
a pressure-measuring layer subjacent to the contact layer and configured to measure pressure from the weight of a human patient, and
a substrate layer having a density and stiffness configured to mechanically isolate the pressure-measuring layer from ambient vibrations transmitted through the floor, furniture, or other intervening articles upon which the multi-layer support surface is mounted;
a processor; and
computer memory having computer-usable instructions stored thereon that when executed by the processor perform operations comprising:

acquire a series of pressure measurements from the measurement device, including pressure measurements received during a first time interval, determine a set of pressure measurement time series including a first time series comprising the pressure measurements received during the first time interval;

determine a multi-taper frequency power spectrum utilizing the first time series, determine a linear regression for each of two piece-wise linear segments of the power spectrum, each of the regressions having a first-order coefficient, based on the regressions, determine a frequency cutpoint where the two piece-wise linear segments join, perform a comparison against noise alpha values utilizing the regression coefficients, based on the comparison, determine a likelihood that the first time period has conditions likely to induce pressure injury, and initiate an action when the determined likelihood exceeds one or more thresholds corresponding with conditions likely to induce pressure injury, wherein the action comprises generating and emitting a notification of an impending deterioration of the patient's condition via a bedside or patient-side alarm, user/clinician interface, or a smartphone or personal computing device of a caregiver.

10. The system of claim 9 wherein the noise alpha values comprise white-, pink-, brown-, and black-noise α values for $1/f^\alpha$ power roll-off.

11. The system of claim 9 wherein the multi-taper frequency power spectrum is determined over a frequency band of 0.003 to 0.1 Hz.

12. The system of claim 9, wherein the pressure measurements acquired from the measurement device are sampled at a rate of at least 20 Hz.

13. The system of claim 9, wherein the first time interval is between 15 and 30 minutes in duration.

14. The system of claim 9 wherein the pressure-measuring layer comprises:
a pressure sensor;
a communication component that receives pressure measurements from the pressure sensor and sends data corresponding to the pressure measurements to the processor or the computer memory,
an air bladder inflatable to hold a volume of air that is in contact with the pressure sensor; and
an inflating mechanism operable to adjust the internal gas pressure of the air bladder.

15. A method for determining a likelihood of a condition for inducing pressure ulcers comprising:
collecting with computer memory or a processor a series of pressure measurements from a measurement device configured to measure pressure from the weight of a human patient, the series of pressure measurements including pressure measurements received during a first time interval and pressure measurements received during one or more previous time intervals;

determining a set of pressure measurement time series including a first time series comprising the pressure measurements received during the first time interval and one or more previous time series corresponding to the pressure measurements received during the one or more previous time intervals;

determining a multi-taper frequency power spectrum utilizing the first time series;

determining a linear regression for each of two piece-wise linear segments of the power spectrum, each of the regressions having a first-order coefficient;

based on the regressions, determining a frequency cut-point where the two piece-wise linear segments join;

comparing the first-order coefficients to characteristic white-, pink-, brown-, and black-noise α values for 1/f* power roll-off with frequency a in a selected range;

based on the comparison, determining a likelihood that the first time period has conditions likely to induce pressure injury; and initiating an action based on the determined likelihood that the first time period has conditions likely to induce pressure injury.

16. The method of claim 15, wherein the selected range of frequency α is between (0.6,+0.4], between (0.4,+1.4], between (1.4,+2.0], and α>+2.0, respectively.

17. The method of claim 15, wherein initiating an action includes generating and emitting a notification of an impending deterioration of the patient's condition via a bedside or patient-side alarm, user/clinician interface, or a smartphone or personal computing device of a caregiver, indicating an elevated risk of pressure injury to the user so as to encourage the user to initiate more frequent movements of positions with respect to the measurement device.

18. The method of claim 15, further comprising:

utilizing the previous time series, determining a duty-cycle of patterns whose frequency spectra are associated with pressure ulcer proneness; and initiating an action when the duty cycle of white-noise spectrum conditions exceeds a threshold value, indicating tissue breakdown and the likelihood of pressure ulcers forming.

19. The system of claim 15, wherein the multi-taper frequency power spectrum is determined over a frequency band of 0.003 to 0.1 Hz.

20. The system of claim 15, wherein the pressure measurements acquired from the measurement device are sampled at a rate of at least 20 Hz.

* * * * *